(12) United States Patent
Igawa et al.

(10) Patent No.: US 10,022,319 B2
(45) Date of Patent: Jul. 17, 2018

(54) STABILIZED ANTIBODY-CONTAINING LIQUID FORMULATIONS

(75) Inventors: Tomoyuki Igawa, Shizuoka (JP); Chifumi Moriyama, Shuzuoka (JP)

(73) Assignee: CHUGAI SEIYAKU KABUSHIKI KAISHA, Tokyo (JP)

(*) Notice: Subject to any disclaimer, the term of this patent is extended or adjusted under 35 U.S.C. 154(b) by 228 days.

(21) Appl. No.: 13/522,848

(22) PCT Filed: Jan. 20, 2011

(86) PCT No.: PCT/JP2011/050911
§ 371 (c)(1),
(2), (4) Date: Oct. 2, 2012

(87) PCT Pub. No.: WO2011/090088
PCT Pub. Date: Jul. 28, 2011

(65) Prior Publication Data
US 2013/0022625 A1    Jan. 24, 2013

(30) Foreign Application Priority Data
Jan. 20, 2010 (JP) ................................ 2010-010060

(51) Int. Cl.
| A61K 39/395 | (2006.01) |
| A61K 9/00 | (2006.01) |
| A61K 47/12 | (2006.01) |
| A61K 47/18 | (2017.01) |

(52) U.S. Cl.
CPC ...... *A61K 9/0019* (2013.01); *A61K 39/39591* (2013.01); *A61K 47/12* (2013.01); *A61K 47/18* (2013.01)

(58) Field of Classification Search
None
See application file for complete search history.

(56) References Cited

U.S. PATENT DOCUMENTS

| 5,795,965 | A | 8/1998 | Tsuchiya et al. |
| 2001/0055617 | A1 | 12/2001 | Mattern et al. |
| 2004/0197324 | A1 | 10/2004 | Liu et al. |
| 2005/0118163 | A1 | 6/2005 | Mizushima et al. |
| 2005/0214278 | A1 | 9/2005 | Kakuta et al. |
| 2007/0036785 | A1 | 2/2007 | Kishimoto et al. |
| 2008/0071063 | A1 | 3/2008 | Allan et al. |
| 2008/0145367 | A1 | 6/2008 | Bove et al. |
| 2009/0291076 | A1 | 11/2009 | Morichika et al. |
| 2009/0324589 | A1 | 12/2009 | Igawa et al. |
| 2010/0028372 | A1* | 2/2010 | Jezek ................... 424/184.1 |
| 2010/0298542 | A1 | 11/2010 | Igawa et al. |
| 2011/0076275 | A1* | 3/2011 | Igawa .............. A61K 39/39591 424/136.1 |
| 2011/0111406 | A1 | 5/2011 | Igawa et al. |

FOREIGN PATENT DOCUMENTS

| CN | 1798575 A | 7/2006 |
| CN | 101166763 A | 4/2008 |
| CN | 101426527 A | 5/2009 |
| EP | 0420649 A2 | 4/1991 |
| EP | 0 783 893 A1 | 7/1997 |
| EP | 1674111 A1 | 6/2006 |
| EP | 1 690 550 A1 | 8/2006 |
| EP | 1 712 237 A2 | 10/2006 |
| EP | 1 712 240 A1 | 10/2006 |
| EP | 2 206 775 A1 | 7/2010 |
| EP | 2 526 963 A1 | 11/2012 |
| JP | 55-102519 A | 8/1980 |
| JP | 2002-505086 A | 2/2002 |
| JP | 2006502116 A | 1/2006 |
| JP | 2006-512087 A | 4/2006 |
| JP | 2007-524602 A | 8/2007 |
| JP | 2007-525171 | 9/2007 |
| JP | 2008-536917 A | 9/2008 |
| JP | 2009-535986 A | 7/2009 |
| JP | 2009539986 A | 11/2009 |

(Continued)

OTHER PUBLICATIONS

Bartelds, G.M., et al., "Clinical response to adalimumab: relationship to anti-adalimumab antibodies and serum adalimumab concentrations in rheumatoid arthritis," *Ann Rheum Dis* 66:921-926, H.K. Lewis, England (2007).
Bender, N. K., et al., "Immunogenicity, efficacy and adverse events of adalimumab in RA patients," *Rheumatol Int* 27:269-274, Springer-Verlag, Germany (2007).
Chirino, A.J., et al., "Minimizing the immunogenicity of protein therapeutics," *DDT* 9(2):82-90, Elsevier Ltd., England (2004).
Dillon, T.M., et al., "Structural and Functional Characterization of Disulfide Isoforms of the Human IgG2 Subclass," *The Journal of Biological Chemistry* 283(23):16205-16215, The American Society for Biochemistry and Molecular Biology, United States (2008).
Gessner, J.E., et al., "The IgG Fc receptor family," *Ann Hematol* 76:231-248, Springer-Verlag, Germany (1998).
Ghetie, V., et al., "Increasing the serum persistence of an IgG fragment by random mutagenesis," *Nature Biotechnology* 15:637-640, Nature America Publishing, United States (1997).

(Continued)

*Primary Examiner* — Yunsoo Kim
(74) *Attorney, Agent, or Firm* — Nixon & Vanderhye P.C.

(57) ABSTRACT

An objective of the present invention is to provide stable antibody-containing formulations which are suitable for subcutaneous administration and in which aggregation formation is suppressed during long-term storage.
The present inventors discovered that a significant stabilization effect was achieved by using an acidic amino acid, aspartic acid or glutamic acid as a counter ion species in histidine buffer or tris(hydroxymethyl)aminomethane, specifically by using histidine-aspartate buffer or histidine-glutamate buffer, or tris(hydroxymethyl)aminomethane-aspartate or tris(hydroxymethyl)aminomethane-glutamate as a buffer. The present inventors also discovered that a significant stabilization effect was achieved by using an acidic amino acid, aspartic acid or glutamic acid, as a counter ion species to a basic amino acid such as arginine, specifically by using arginine-aspartate or arginine-glutamate.

17 Claims, 24 Drawing Sheets

(56) References Cited

FOREIGN PATENT DOCUMENTS

| | | |
|---|---|---|
| KR | 10-2007-0068385 | 6/2007 |
| KR | 10-2008-0098504 | 11/2008 |
| RU | 2191003 C2 | 8/2000 |
| TW | 201138828 A1 | 11/2011 |
| WO | WO 92/19759 A1 | 11/1992 |
| WO | WO 96/11020 A1 | 4/1996 |
| WO | WO 96/12503 A1 | 5/1996 |
| WO | WO 97/04801 A1 | 2/1997 |
| WO | WO 99/43713 A1 | 9/1999 |
| WO | WO 03/068259 A1 | 8/2003 |
| WO | WO 03/068260 A1 | 8/2003 |
| WO | WO-2004007520 A | 1/2004 |
| WO | WO 2004/035752 A2 | 4/2004 |
| WO | WO 2004/055164 A2 | 7/2004 |
| WO | WO 2004/091658 A1 | 10/2004 |
| WO | WO 2004/092219 A2 | 10/2004 |
| WO | WO 2004/096273 A1 | 11/2004 |
| WO | WO 2005/063291 A1 | 7/2005 |
| WO | WO-2006006693 A1 | 1/2006 |
| WO | WO 2006/044908 A2 | 4/2006 |
| WO | WO 2006/065746 A2 | 6/2006 |
| WO | WO 2006/112838 A1 | 10/2006 |
| WO | WO 2007/074880 A1 | 7/2007 |
| WO | WO 2007/092772 A2 | 8/2007 |
| WO | WO-2007109221 A2 | 9/2007 |
| WO | WO 2007/114319 A1 | 10/2007 |
| WO | WO 2007/143168 A2 | 12/2007 |
| WO | WO-2007146268 A | 12/2007 |
| WO | WO 2008/045373 A2 | 4/2008 |
| WO | WO 2008/071394 A1 | 6/2008 |
| WO | WO 2008/079290 A2 | 7/2008 |
| WO | WO 2008/084237 A2 | 7/2008 |
| WO | WO 2008/116103 A2 | 9/2008 |
| WO | WO 2008/121615 A2 | 10/2008 |
| WO | WO 2009/041613 A1 | 4/2009 |
| WO | WO 2009/041621 A1 | 4/2009 |
| WO | WO 2009/041643 A1 | 4/2009 |
| WO | WO-2009072604 A1 | 6/2009 |
| WO | WO 2009/086400 A2 | 7/2009 |
| WO | WO 2009/125825 A1 | 10/2009 |
| WO | WO 2009/141239 A1 | 11/2009 |
| WO | WO 2010/106812 A1 | 9/2010 |

OTHER PUBLICATIONS

Hinton, P.R., et al., "An Engineered Human IgG1 Antibody with Longer Serum Half-Life," *Journal of Immunology* 176:346-356, The American Association of Immunologists, United States (2006).

Hwang, W.Y.K., et al., "Use of human germline genes in a CDR homology-based approach to antibody humanization," *Methods* 36:35-42, Elsevier Inc., United States (2005).

Ishihara, T., et al., "Accelerated purification process development of monoclonal antibodies for shortening time to clinic Design and case study of chromatography processes," *Journal of Chromatography A* 1176:149-156, Elsevier B.V., Netherlands (2007).

Ito, W., et al., "The His-probe method: effects of histidine residues introduced into the complementary-determining regions of antibodies on antigen-antibody interactions at different pH values," *FEBS* 309(1):85-88, Elsevier Science Publishers B.V., Netherlands (1992).

Johnson, K.A., et al., "Cation exchange-HPLC and mass spectrometry reveal C-terminal amidation of an IgG1 heavy chain," *Analytical Biochemistry* 360:75-83, Elsevier Inc., United States (2007).

Jones, T.D., et al., "Identification and removal of a promiscuous CD4+ T cell epitope from the C1 domain of factor VIII," *J Thromb Haemost* 3:991-1000, International Society on Thrombosis and Haemostasis, United States (2005).

Kim, S.J., et al., "Antibody Engineering for the Development of Therapeutic Antibodies," *Mol Cells* 20(1):17-29, KSMCB, South Korea (2005).

Maini, R.N., et al., "Double-Blind Randomized Controlled Clinical Trial of the Interleukin-6 Receptor Antagonist, Tocilizumab, in European Patients With Rheumatoid Arthritis Who Had an Incomplete Response to Methotrexate," *Arthritis and Rheumatism* 54(9):2817-2829, American College of Rheumatology, United States (2006).

Nishimoto, N., et al., "Anti-interleukin 6 receptor antibody treatment in rheumatic disease," *Ann Rheum Dis* 59(*suppl* 1):i21-i27, H.K. Lewis, England (2000).

Nishimoto, N., et al., "Humanized anti-interleukin-6 receptor antibody treatment of multicentric Castleman disease," *Blood* 106(8):2627-2632, The American Society of Hematology, United States (2005).

Nishimoto, N., et al., "Interleukin 6: from bench to bedside," *Nature Clinical Practice Rheumatology* 2(11):619-626, Nature Publishing Group, United States (2006).

Nishimoto, N., et al., "Humanized anti-IL-6 Receptor Antibody (Tocilizumab)," *Nihon Rinsho* 65(7):1218-1225, Nihon Rinsho Co, Japan (2007).

Nishimoto, N. and Kishimoto, T., "Humanized Antihuman IL-6 Receptor Antibody Tocilizumab," *Therapeutic Antibodies Handbook of Experimental Pharmacology* 181:151-160, Spinger-Verlag, Germany (2008).

Onda, M., et al., "Lowering the Isoelectric Point of the Fv Portion of Recombinant Immunotoxins Leads to Decreased Nonspecific Animal Toxicity without Affecting Antitumor Activity," *Cancer Research* 61:5070-5077, American Association for Cancer Research, United States (2001).

Pavlou, A.K. and Belsey, M.J., "The therapeutic antibodies market to 2008," *European Journal of Pharmaceutics and Biopharmaceutics* 59:389-396, Elsevier B.V., Netherlands (2005).

Philippovich, Y.B. *Fundamentals of Biochemistry*, edition Higher school, p. 31, Moscow (1969).

Pokrovsky, V.I., ed., *Soviet Encyclopedia*, p. 146 (1991).

Rajpal, A., et al., "A general method for greatly improving the affinity of antibodies by using combinatorial libraries," *PNAS* 102(24):8466-8471, The National Academy of Sciences of the USA, United States (2005).

Reichert, J.M., et al., "Monoclonal antibody successes in the clinic," *Nature Biotechnology* 23(9):1073-1078, Nature America Publishing, United States (2005).

Rothe, A., et al., "Ribosome display for improved biotherapeutic molecules," *Expert Opin. Biol. Ther.* 6(2):177-187, Ashley Publications Ltd., England (2006).

Salfeld, J.G., "Isotype selection in antibody engineering," *Nature Biotechnology* 25(12):1369-1372, Nature America Publishing, United States (2007).

Sato, K., et al., "Reshaping a Human Antibody to Inhibit the Interleukin 6-dependent Tumor Cell Growth," *Cancer Research* 53:851-856, American Association for Cancer Research, United States (1993).

Strand, V., et al., "Biologic therapies in rheumatology: lessons learned, future doctors," *Nature Reviews Drug Discovery* 6:75-92, Nature Publishing Group, England (2007).

Van Walle, I., et al., "Immunologenicity screening in protein drug development," *Expert Opin. Biol. Ther.* 7(3):405-418, Informa UK Ltd, Great Britain (2007).

Wu, H., et al., "Development of Motavizumab, an Ultra-potent Antibody for the Prevention of Respiratory Syncytial Virus Infection in the Upper and Lower Respiratory Tract," *J. Mol. Bio.* 368:652-665, Elsevier Ltd., England (2007).

Daugherty, A.L., and Mrsny, R.J., "Formulation and delivery issues for monoclonal antibody therapeutics," *Advanced Drug Delivery Reviews* 58:686-706, Elsevier B.V., Netherlands (2006)

Shire, S.J., et al., "Challenges in the Development of High Protein Concentration Formulations," *Journal of Pharmaceutical Sciences* 93(6):1390-1402, Wiley-Liss, Inc. and the American Pharmacists Association, United States (2004).

Shire, S.J., "Formulation and manufacturability of biologics," *Current Opinion in Biotechnology* 20:708-714, Elsevier Ltd., England (2009).

Wang, W., et al., "Antibody Structure, Instability, and Formulation," *Journal of Pharmaceutical Sciences* 96(1):1-26, Wiley-Liss, Inc. and the American Pharmacists Association, United States (2007).

(56) References Cited

OTHER PUBLICATIONS

English language translation (unverified) of Patent Application No. WO 2009/041621 A1, Chugai Seiyaku Kabushiki Kaisha, published Apr. 2, 2009.
International Search Report for International Application No. PCT/JP2011/050911, Japanese Patent Office, Japan, dated Mar. 22, 2011.
Gokarn, Y.R. et al., "Self-Buffering Antibody Formulations," *Journal of Pharmaceutical Sciences* 97(8):3051-3066, Wiley-Liss, Inc. and the American Pharmacists Association, United States (2008).

* cited by examiner

STABILIZED ANTIBODY-CONTAINING LIQUID FORMULATIONS

REFERENCE TO SEQUENCE LISTING SUBMITTED ELECTRONICALLY

The content of the electronically submitted sequence listing (Name: 21440640001_SEQ_LST.text; Size: 12,088 bytes; and Date of Creation: Jul. 13, 2012) filed with the application is incorporated herein by reference in its entirety.

TECHNICAL FIELD

The present invention relates to antibody-containing formulations, in particular to stable highly-concentrated antibody-containing formulations.

BACKGROUND ART

In recent years, there is an increasing demand for developing self-injectable antibody-containing formulations for subcutaneous injection according to medical needs. Designing antibody-containing formulations for subcutaneous injection makes it necessary to increase the antibody concentration in the administered solution, since a single doses of antibody are very high (about 100 to 200 mg) and the injection volume for subcutaneous injection is generally limited.

Highly-concentrated antibody-containing solutions tend to form highly viscous solutions by themselves due to intermolecular interactions and macromolecular protein characteristics. Furthermore, degradation phenomenon such as aggregation becomes problematic when proteins are stored as highly-concentrated solutions, and thus, this degradation must be prevented. In particular, highly-concentrated antibody-containing solutions tend to form aggregates during freeze-thawing, or when stored in liquid or frozen conditions for a long time (Non-patent Documents 1 and 2).

To date, such highly-concentrated antibody-containing formulations are generally prepared by conventional lyophilizing concentration method (Patent Document 1), which is a method for stabilizing highly-concentrated antibody-containing formulations. In the method, highly-concentrated antibody-containing formulations are obtained by lyophilizing an antibody solution of a relatively low concentration and dissolving in a smaller volume of water than the volume before lyophilization. In this case, the increased viscosity of dissolved formulations is of concern because a cryoprotectant such as sugar must be added to obtain lyophilized formulations.

In that aspect, this problem can be avoided when a liquid formulation is prepared without lyophilization. However, as described above, highly-concentrated antibody-containing liquid formulations tend to form aggregates. Nonetheless, such formulations are highly demanded because antibody-containing liquid formulations are easier to handle than lyophilized formulations, and can be readily formulated into prefilled syringe formulations.

There have been various studies to stabilize highly-concentrated antibody-containing liquid formulations (Non-patent Documents 1-4). Histidine buffer and arginine have been reported to be useful as a buffer and a stabilizer, respectively, in antibody-containing liquid formulations (Patent Documents 2, 3, 4, 5, and 6). The histidine buffer is commonly used in the form of hydrochloric acid salt. Recently, it has been reported that histidine-acetate shows a higher stabilization effect than histidine hydrochloride and thus acetic acid is useful as a counter ion species in histidine buffer (Patent Document 6). Meanwhile, arginine as a stabilizer has been generally used in the form of arginine hydrochloride. However, in some cases, sufficient stability is not obtained when hydrochloric acid or acetic acid is used as a counter ion species to histidine or arginine. Thus, more superior counter ion species are needed.

PRIOR ART DOCUMENTS

Patent Documents

Patent Document 1: WO 1997/004801
Patent Document 2: WO 2008/121615
Patent Document 3: WO 2009/141239
Patent Document 4: WO 2008/071394
Patent Document 5: WO 2006/065746
Patent Document 6: WO 2006/044908

Non-Patent Documents

Non-patent Document 1: Challenges in the development of high protein concentration formulations, J Pharm Sci, 2004, 93 (6), 1390-1402
Non-patent Document 2: Curr Opin Biotechnol. 2009 December; 20(6):708-14. Epub 2009 Oct. 31
Non-patent Document 3: Antibody structure, instability, and formulation, J Pharm Sci, 2007, 96 (1), 1-26
Non-patent Document 4: Formulation and delivery issues for monoclonal antibody therapeutics, Adv Drug Del Rev, 2006, 58 (5-6), 686-706

DISCLOSURE OF THE INVENTION

Problems to be Solved by the Invention

An objective of the present invention is to provide stable highly-concentrated antibody-containing formulations which are suitable for subcutaneous administration.

Means for Solving the Problems

To achieve the above-described objective, the present inventors conducted dedicated studies. As a result, the present inventors discovered that a significantly higher stabilization effect was achieved by using an acidic amino acid, aspartic acid or glutamic acid as a counter ion species in histidine buffer or tris(hydroxymethyl)aminomethane buffer, i.e., histidine-aspartate buffer or histidine-glutamate buffer, or tris(hydroxymethyl)aminomethane-aspartate buffer or tris(hydroxymethyl)aminomethane-glutamate buffer as compared to conventionally reported buffers for pharmaceutical formulations such as histidine hydrochloride buffer and histidine-acetate buffer. The present inventors also discovered that a significantly higher stabilization effect was achieved by using arginine-aspartate or arginine-glutamate as a stabilizer, i.e., by using an acidic amino acid, aspartic acid or glutamic acid as a counter ion species to a basic amino acid such as arginine which is used as a stabilizer as compared to conventionally reported stabilizers for pharmaceutical formulations such as arginine hydrochloride. Thus, the present inventors discovered that stable highly-concentrated antibody-containing liquid formulations can be obtained by adding them as a stabilizer and thereby completed the present invention.

Specifically, the present invention provides:

[1] a stable antibody-comprising formulation comprising basic amino acid-aspartate or basic amino acid-glutamate;
[2] the formulation of [1] comprising histidine-aspartate buffer or histidine-glutamate buffer, wherein the basic amino acid is histidine;
[3] the formulation of [1] comprising arginine-aspartate or arginine-glutamate, wherein the basic amino acid is arginine;
[4] a stable antibody-comprising formulation comprising histidine-aspartate buffer or histidine-glutamate buffer, and arginine-aspartate or arginine-glutamate;
[5] a stable antibody-comprising formulation comprising tris(hydroxymethyl)aminomethane-aspartate buffer or tris(hydroxymethyl)aminomethane-glutamate buffer;
[6] a stable antibody-comprising formulation comprising tris(hydroxymethyl)aminomethane-aspartate buffer and tris(hydroxymethyl)aminomethane-glutamate buffer;
[7] the formulation according to any one of [1] to [6], which does not substantially comprise chloride ion and acetate ion;
[8] the formulation according to any one of [1] to [7], which additionally comprises a sugar;
[9] the formulation according to any one of [1] to [8], wherein the antibody is a humanized antibody or a human antibody;
[10] the formulation according to any one of [1] to [9], wherein the antibody has been modified to have an isoelectric point (pI) of 5 to 8;
[11] the formulation according to any one of [1] to [10], wherein the antibody concentration is 50 mg/ml or more;
[12] the formulation according to any one of [1] to [10], wherein the antibody concentration is 50 to 250 mg/ml;
[13] the formulation according to any one of [1] to [12], which is a liquid formulation;
[14] the formulation according to [13], wherein the viscosity of the liquid formulation is 30 mPa·s or less;
[15] the formulation according to [13] or [14], wherein the liquid formulation is stable at 2° C. to 8° C. for at least six months;
[16] the formulation according to any one of [13] to [15], which has not been subjected to lyophilization during preparation of the formulation;
[17] the formulation according to any one of [13] to [16], which is frozen stored at −30° C. to −10° C.;
[18] the formulation according to any one of [1] to [12], wherein the formulation is a lyophilized formulation;
[19] the formulation according to any one of [2], [4], and [7] to [18], wherein the buffer concentration is 5 to 100 mM;
[20] the formulation according to any one of [3] and [7] to [19], wherein the arginine concentration is 5 to 300 mM;
[21] the formulation according to any one of [1] to [20], wherein the antibody is an anti-IL-6 receptor antibody;
[22] the formulation according to any one of [2], [4], and [7] to [21], wherein the buffer substantially comprises only amino acid(s);
[23] the formulation according to any one of [1] to [22], which is for subcutaneous administration;
[24] a method for suppressing aggregation formation during frozen storage of a highly-concentrated antibody-comprising formulation by using aspartic acid or glutamic acid as a counter ion species to a buffer in the formulation;
[25] a method for suppressing aggregation formation during liquid storage of a highly-concentrated antibody-comprising formulation by using aspartic acid or glutamic acid as a counter ion species to a buffer in the formulation;
[26] a method for suppressing aggregation formation during frozen storage of a highly-concentrated antibody-comprising formulation by using aspartic acid or glutamic acid as a counter ion species to a stabilizer in the formulation; and
[27] a method for suppressing aggregation formation during liquid storage of a highly-concentrated antibody-comprising formulation by using aspartic acid or glutamic acid as a counter ion species to a stabilizer in the formulation.

Furthermore, the present invention relates to use of basic amino acid-aspartate or basic amino acid-glutamate in manufacturing a stable antibody-comprising formulation; and aspartic acid or glutamic acid as a counter ion species to a buffer or stabilizer in a highly-concentrated antibody-comprising formulation, used in a method for suppressing aggregation during frozen storage or liquid storage of the formulation.

Effects of the Invention

The present invention provides antibody-containing formulations that are superior in stability. The present invention can also provide highly-concentrated antibody-containing formulations by suppressing the aggregation formation in liquid and frozen formulations. The highly-concentrated antibody-containing formulations of the present invention can be stably stored in liquid or in frozen condition for a long period. Furthermore, the formulations of the present invention have an improved stability against freeze-thawing stress. In addition, in terms of osmotic pressure, stabilization can be achieved without increasing osmotic pressure, by using aspartic acid and glutamic acid rather than the conventionally used hydrochloric acid and acetic acid as counter ion species to histidine, arginine, or tris(hydroxymethyl)aminomethane. It is advantageous to achieve stabilization without increasing the osmotic pressure, when one intends to produce almost isotonic, stable formulations, such as formulations for subcutaneous (SC) administration.

MODE FOR CARRYING OUT THE INVENTION

Figure 1:
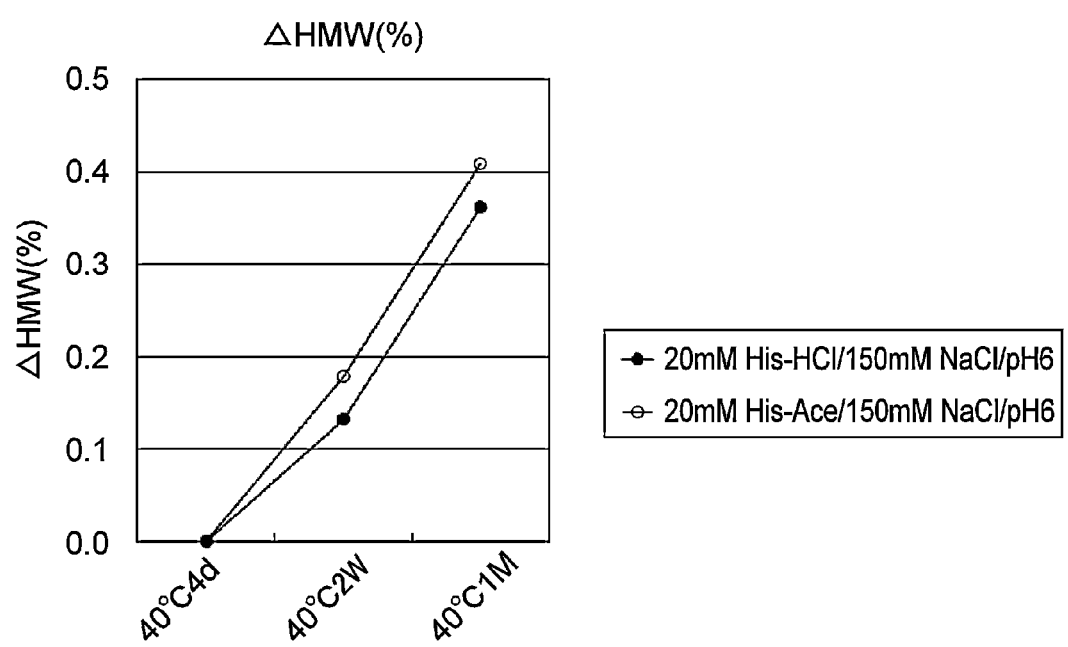
FIG. 1 is a graph plotted with time-dependent changes of the amount (%) of aggregate during storage of Mab1 at 40° C. on the vertical axis.

Hereinbelow, the present invention will be described more specifically.

The present invention provides stable antibody-containing formulations which contain basic amino acid-aspartate or basic amino acid-glutamate. In the present invention, basic amino acids include, for example, histidine, arginine, and lysine. Furthermore, in the present invention, buffers of basic amino compounds such as tris(hydroxymethyl)aminomethane are also included in the definition of the basic amino acids of the present invention.

Specifically, the present invention provides stable antibody-containing formulations which contain histidine-aspartate buffer or histidine-glutamate buffer where the basic amino acid is histidine. Furthermore, the present invention provides stable antibody-containing formulations which contain arginine-aspartate or arginine-glutamate as a stabilizer, where the basic amino acid is arginine. The present invention also provides stable antibody-containing formulations which contain histidine-aspartate buffer or histidine-glutamate buffer, and arginine-aspartate or arginine-glutamate. Furthermore, the present invention provides stable antibody-containing formulations which contain tris(hydroxymethyl)aminomethane-aspartate buffer or tris(hydroxymethyl)aminomethane-glutamate buffer. The present invention also provides stable antibody-containing formulations which contain tris(hydroxymethyl)aminomethane-aspartate buffer and tris(hydroxymethyl)aminomethane-glutamate buffer. The antibody-containing formulation of the present invention refers to a formulation that contains an antibody as an active ingredient and is prepared in a form that allows administration to animals such as human.

Herein, "stable antibody-containing formulation" refers to a formulation in which aggregation of proteins such as antibody is hardly formed, specifically, a formulation in which degradation such as formation of insoluble and soluble aggregates hardly occurs during storage in liquid or in frozen condition.

The concentration of antibody in a formulation of the present invention is not particularly limited; however, the formulation preferably contains a high concentrated antibody. The antibody concentration is preferably 50 mg/ml or more, more preferably 100 mg/ml or more, even more preferably 120 mg/ml or more, still more preferably 150 mg/ml or more, and yet more preferably 180 mg/ml or more. The upper limit of the antibody concentration in a formulation of the present invention is not particularly limited; however, the limit is generally 250 mg/ml.

The antibodies used in the present invention are not particularly limited, as long as they bind to an antigen of interest. The antibodies may be polyclonal or monoclonal antibodies; however, monoclonal antibodies are preferred because they can be stably produced as homogeneous antibodies.

The monoclonal antibodies used in the present invention include not only those derived from animals such as humans, mice, rats, hamsters, rabbits, sheep, camels, and monkeys, but also artificially modified gene recombinant antibodies such as chimeric antibodies, humanized antibodies, and bispecific antibodies. The antibodies of the present invention also include gene recombinant antibodies that result from artificially modifying the antibody constant regions to alter the physical properties of the antibody molecule (specifically, alteration of the isoelectric point (pI), improvement of the affinity for Fc receptor, etc) for the purpose of improving the blood persistence and in vivo pharmacokinetics.

The immunoglobulin class of the antibodies used in the present invention is not particularly limited; and the class may be any class, including IgG such as IgG1, IgG2, IgG3, and IgG4, IgA, IgD, IgE, and IgM. However, IgG and IgM are preferred.

The antibodies used in the present invention also include not only whole antibodies but also antibody fragments such as Fv, Fab, and F(ab)$_2$, and minibodies (low molecular weight antibodies) such as monovalent or bivalent single-chain Fv that result from linking antibody variable regions via a linker such as peptide linker (scFv, sc(Fv)$_2$, diabodies such as scFv dimer, etc).

The above-described antibodies used in the present invention can be prepared by methods known to those skilled in the art.

Basically, monoclonal antibody-producing hybridomas can be prepared by the conventional methods described below. Specifically, immunization is carried out by a conventional immunization method using a desired antigen or cells expressing the desired antigen as a sensitizing antigen. The prepared immunocytes are fused with known parental cells by a conventional cell fusion method. The fused cells are screened for monoclonal antibody-producing cells (hybridomas) by conventional screening methods. Hybridomas can be generated, for example, according to the method of Milstein et al. (Kohler, G. and Milstein, C., Methods Enzymol. (1981) 73:3-46). When an antigen has low immunogenicity, immunization can be performed using the antigen linked to immunogenic macromolecules such as albumin.

Alternatively, it is possible to use gene recombinant antibodies produced using gene recombination techniques in which antibody genes are cloned from hybridomas and inserted into appropriate vectors, and the resulting vectors are introduced into hosts (see, for example, Carl, A. K. Borrebaeck, James, W. Larrick, Therapeutic Monoclonal Antibodies, Published in the United Kingdom by Macmillan Publishers, 1990). Specifically, cDNAs for antibody variable regions (V regions) are synthesized from the mRNAs of hybridomas using reverse transcriptase. When a DNA encoding an antibody V region of interest is obtained, the DNA is linked to a DNA encoding a desired antibody constant region (C region). The resulting construct is inserted into an expression vector. Alternatively, the antibody V region-encoding DNA may be inserted into an expression vector carrying the DNA of the antibody C region. The resulting construct is inserted into an expression vector so that it is expressed under the control of an expression regulatory region, for example, enhancer and promoter. Then, host cells are transformed with the expression vector to express the antibody.

In the present invention, artificially modified gene recombinant antibodies such as chimeric and humanized antibodies can be used to reduce heterologous antigenicity against human. Such modified antibodies can be produced using known methods. A chimeric antibody is an antibody having the heavy-chain and light-chain variable regions of an antibody from a nonhuman mammal such as mouse, and the heavy-chain and light-chain constant regions of a human antibody. The chimeric antibody can be produced by linking a DNA encoding the variable regions of a mouse antibody to a DNA encoding the constant regions of a human antibody, inserting the ligate into an expression vector, and then introducing the vector into a host for expression.

A humanized antibody is also referred to as reshaped human antibody, and is obtained by substituting the complementarity determining region (CDR) of a human antibody for the complementarity determining region of an antibody derived from a nonhuman mammal, for example, mouse. Conventional gene recombination techniques are known. Specifically, a DNA sequence is designed to have a mouse antibody CDR linked to a human antibody framework (FR) region, and is synthesized by PCR using several oligonucleotides prepared to have overlapping regions at their ends. The obtained DNA is ligated to a DNA encoding a human antibody constant region and then inserted into an expression vector. The expression vector is introduced into a host to produce the humanized antibody (see, European Patent Application Publication No. EP 239400 and WO 96/02576). The CDR-linked human antibody FR is selected so that the complementarity determining region forms a preferable antigen-binding domain. Amino acids in the framework region of the antibody variable region can be substituted as required so that the complementarity determining region of the reshaped human antibody forms a suitable antigen-binding domain (Sato, K. et al., Cancer Res. (1993) 53, 851-856).

There are known techniques for substituting amino acids in antibodies to improve antibody activities, physical properties, pharmacokinetics, safety, and such. Examples of such techniques are described below. The antibodies of the present invention also include those having such amino acid substitutions.

Techniques are reported for substituting amino acids in the IgG antibody variable regions, and include humanization (Tsurushita N, Hinton P R, Kumar S., Design of humanized antibodies: from anti-Tac to Zenapax., Methods. 2005 May; 36(1):69-83); affinity maturation to enhance the binding activity via amino acid substitution in the complementarity determining region (CDR) (Rajpal A, Beyaz N, Haber L, Cappuccilli G, Yee H, Bhatt R R, Takeuchi T, Lerner R A, Crea R., A general method for greatly improving the affinity of antibodies by using combinatorial libraries., Proc Natl Acad Sci USA. 2005 Jun. 14; 102(24):8466-71); and improvement of physicochemical stability via amino acid substitution in the framework (FR) (Ewert S, Honegger A, Pluckthun A., Stability improvement of antibodies for extracellular and intracellular applications: CDR grafting to stable frameworks and structure-based framework engineering., Methods. 2004 October; 34(2):184-99. Review). There are also known techniques for enhancing antibody-dependent cell cytotoxicity (ADCC) and complement-dependent cytotoxicity (CDC) by substituting amino acids in IgG antibody Fc domain (Kim S J, Park Y, Hong H J., Antibody engineering for the development of therapeutic antibodies., Mol Cells. 2005 Aug. 31; 20(1):17-29. Review). Furthermore, in addition to techniques for enhancing the effector functions, there are reports published on techniques for improving the antibody half-life in blood by substituting amino acids in Fc (Hinton P R, Xiong J M, Johlfs M G, Tang M T, Keller S, Tsurushita N., An engineered human IgG1 antibody with longer serum half-life., J Immunol. 2006 Jan. 1; 176(1):346-56; Ghetie V, Popov S, Borvak J, Radu C, Matesoi D, Medesan C, Ober R J, Ward E S., Increasing the serum persistence of an IgG fragment by random mutagenesis., Nat. Biotechnol. 1997 July; 15(7):637-40). Another known technique includes amino acid substitution technique to control the isoelectric point (pI) of an antibody for the purpose of improving the blood persistence or in vivo pharmacokinetics, specifically, a technique for modifying amino acid residues exposed on the surface of an antibody to control the pI of the antibody (WO 07/114,319). Various techniques to substitute amino acids in the constant regions for the purpose of improving the physical properties of an antibody are also known (WO 09/41613).

Reduction of the dosage of antibody as a pharmaceutical or extension of the interval of antibody administration can be expected by extending the half-life or plasma retention of an antibody. Promising technologies to achieve this include a technique for decreasing the isoelectric point of antibody (WO 07/114,319). The formulations of the present invention have a high stabilizing effect for antibodies with an altered isoelectric point. The pI-modified antibody refers to a modified antibody whose pI is lower than that of the original antibody by one or more, preferably two or more, and more preferably three or more. In general, natural (or ordinary) antibodies are assumed to have an isoelectric point within the range of 7.5 to 9.5. The formulations of the present invention have a high stabilizing effect for, in particular, antibodies with a low isoelectric point which hardly exist in nature. The isoelectric point of such antibodies may be 5.0 to 8.0, preferably 5.0 to 7.5, more preferably 5.0 to 7.0, and still more preferably 5.5 to 6.5. As described in the Examples below, the isoelectric point of Mab1, which was produced from modification of the Mab2 (isoelectric point=9.3) amino acid sequence to control the isoelectric point, was 5.8.

Methods for obtaining human antibodies are also known. For example, desired human antibodies with antigen-binding activity can be obtained by sensitizing human lymphocytes with an antigen of interest or cells expressing an antigen of interest in vitro; and fusing the sensitized lymphocytes with human myeloma cells such as U266 (see Japanese Patent Application Kokoku Publication No. (JP-B) H01-59878 (examined, approved Japanese patent application published for opposition)). Alternatively, desired human antibodies can also be obtained by immunizing transgenic animals having the entire repertoire of human antibody genes with an antigen (see WO 93/12227, WO 92/03918, WO 94/02602, WO 94/25585, WO 96/34096, and WO 96/33735). Furthermore, techniques for obtaining human antibodies by panning with a human antibody library are known. For example, the variable regions of human antibodies can be expressed as single-chain antibodies (scFvs) on the surface of phages using a phage display method, and then phages that bind to the antigen can be selected. The genes of selected phages can be analyzed to determine the DNA sequences that encode the variable regions of human antibodies that bind to the antigen. When the DNA sequences of scFvs that bind to the antigen are identified, appropriate expression vectors carrying these sequences can be constructed to obtain human antibodies. Such methods are already well known. See WO 92/01047, WO 92/20791, WO 93/06213, WO 93/11236, WO 93/19172, WO 95/01438, and WO 95/15388. The antibodies used in the present invention also include such human antibodies.

When the antibody genes are isolated and introduced into appropriate hosts to produce antibodies, hosts and expression vectors can be used in appropriate combinations. When eukaryotic cells are used as a host, animal cells, plant cells, and fungal cells can be used. The animal cells include: (1) mammalian cells such as CHO, COS, myeloma, baby hamster kidney (BHK), HeLa, and Vero cells; (2) amphibian cells such as *Xenopus* oocytes; and (3) insect cells such as sf9, sf21, and Tn5. Known plant cells include cells derived from genus *Nicotiana* such as *Nicotiana tabacum*, which can be cultured as a callus. Known fungal cells include yeasts such as genus *Saccharomyces*, for example *Saccharomyces cerevisiae*, and filamentous fungi such as genus *Aspergillus*, for example *Aspergillus niger*. When using prokaryotic cells, production systems using bacterial cells can be used. Known bacterial cells include *Escherichia coli* (*E. coli*) and *Bacillus subtilis*. The antibodies can be obtained by introducing the antibody genes of interest into these cells by transformation and then culturing the transformed cells in vitro.

The antibodies used in the present invention also include antibody fragments, minibodies, and modified antibodies. Such antibody fragments and minibodies include, for example, Fab, F(ab')2, Fv, or mono-, bi-, or multi-valent single-chain Fv (scFv, sc(Fv)$_2$, or such) resulting from linking H chain and L chain Fvs via appropriate linkers (Huston J. S. et al., (1988) Proc. Natl. Acad. Sci. U.S.A. 85:5879-5883). Specifically, such antibody fragments are generated by treating antibodies with an enzyme such as papain or pepsin. Alternatively, the gene encoding an antibody fragment is constructed, inserted into an expression vector, and expressed in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Modified antibodies include antibodies linked to polyethylene glycol (PEG) or various molecules such as cytotoxic agents (Farmaco. 1999 Aug. 30; 54(8):497-516; Cancer J. 2008 May-June; 14(3):154-69). The "antibodies" of the present invention also include such modified antibodies. Such modified antibodies can be prepared by chemically modifying the obtained antibodies. Such methods are already established in this field.

Antibodies to be contained in formulations of the present invention include, but are not limited to, anti-tissue factor antibodies, anti-IL-6 receptor antibodies, anti-IL-6 antibodies, anti-HM1.24 antigen monoclonal antibodies, anti-parathyroid hormone-related peptide antibodies (anti-PTHrP antibodies), anti-glypican-3 antibodies, anti-ganglioside GM3 antibodies, anti-TPO receptor agonist antibodies, antibodies as a functional substitute for coagulation factor VIII, anti-IL31 receptor antibodies, anti-HLA antibodies, anti-AXL antibodies, anti-CXCR4 antibodies, anti-NR10 antibodies, and bispecific antibodies against factor IX and factor X.

Preferred reshaped humanized antibodies used in the present invention include humanized interleukin 6 (IL-6) receptor antibodies (tocilizumab, hPM-1, and MRA) (see WO 92/19759), humanized anti-HM1.24 antigen monoclonal antibodies (see WO 98/14580), humanized anti-parathyroid hormone-related peptide antibodies (anti-PTHrP antibodies) (see WO 98/13388), humanized anti-tissue factor antibodies (see WO 99/51743), humanized anti-glypican-3 IgG1κ antibodies (see PCT/JP05/013103), and anti-NR10 humanized antibodies (see WO2009/072604). Particularly preferred humanized antibodies used in the present invention are humanized anti-IL-6 receptor antibodies.

Preferred human IgM antibodies include recombinant human anti-ganglioside GM3 IgM antibodies (see WO 05/05636).

Preferred minibodies include anti-TPO receptor agonist diabodies (see WO 02/33072) and anti-CD47 agonist diabodies (see WO 01/66737).

Furthermore, antibodies with an improved isoelectric point include, for example, Mab1 (H chain/SEQ ID NO: 1; L chain/SEQ ID NO: 2), which is an anti-IL-6 receptor antibody described in WO 2009/041621, anti-NR10 humanized antibodies, and fully humanized NS22 antibodies produced by the method described in Example 12 of WO2009/072604.

In a preferred embodiment, the buffer of a formulation of the present invention (for example, histidine-aspartate buffer, histidine-glutamate buffer, tris(hydroxymethyl)aminomethane-aspartate buffer, or tris(hydroxymethyl)aminomethane-glutamate buffer) is prepared by titrating an aqueous solution containing basic amino acid such as histidine or tris(hydroxymethyl)aminomethane as a free amino acid with an aqueous solution containing aspartic acid and/or glutamic acid as a free amino acid. Alternatively, the buffer can be prepared by adding the ingredients in the reverse order, or by direct titration with powders.

In a preferred embodiment, arginine-aspartate or arginine-glutamate in a formulation of the present invention is a salt prepared by titrating an aqueous solution containing aspartic acid (free amino acid) and/or glutamic acid (free amino acid)

as a free amino acid with an aqueous solution containing arginine (free base) as a free amino acid. Alternatively, the salt can be prepared by adding the ingredients in the reverse order, or by direct titration with powders.

The present inventors conducted freeze-thawing study, thermal acceleration study, long term stability study, and frozen storage study to assess the effects of various additives on the stability of highly-concentrated antibody formulations during storage. As a result, the present inventors discovered that the aggregation formation was significantly suppressed by using an acidic amino acid, aspartic acid or glutamic acid as a counter ion species in histidine buffer, i.e., by using histidine-aspartate buffer or histidine-glutamate buffer as a buffer as compared to conventional buffers for pharmaceutical formulations such as histidine hydrochloride buffer and histidine-acetate buffer.

The present inventors also discovered that a higher stabilization effect was achieved by adding arginine-aspartate or arginine-glutamate as compared to arginine hydrochloride which has been reported as a stabilizer for antibody-containing formulations. The assessment results are exemplified in the Examples hereinbelow, using a humanized anti-IL-6 receptor antibody.

Specifically, stable highly-concentrated antibody-containing formulations that have low levels of antibody aggregation can be prepared by adding histidine-aspartate buffer or histidine-glutamate buffer, or tris(hydroxymethyl)aminomethane-aspartate buffer or tris(hydroxymethyl)aminomethane-glutamate buffer. Furthermore, more stable highly-concentrated antibody-containing formulations that have much lower levels of antibody aggregation can be prepared by adding arginine-aspartate or arginine-glutamate as a stabilizer. Thus, the present invention relates to methods for significantly suppressing the aggregation formation by using histidine-aspartate buffer or histidine-glutamate buffer, or tris(hydroxymethyl)aminomethane-aspartate buffer or tris(hydroxymethyl)aminomethane-glutamate buffer as a buffer for highly-concentrated antibody-containing solutions, and methods for significantly suppressing the aggregation formation by adding arginine-aspartate or arginine-glutamate as a stabilizer to highly-concentrated antibody-containing solutions.

In an embodiment, the methods of the present invention include, for example, methods for suppressing the aggregation formation during storage of highly-concentrated antibody-containing formulations under frozen conditions or freeze-thawing by using aspartic acid or glutamic acid as a counter ion species to the buffer (for example, histidine buffer or tris(hydroxymethyl)aminomethane buffer) or as a counter ion species to the stabilizer (for example, arginine) in the formulations.

In another embodiment, the methods of the present invention include, for example, methods for suppressing the aggregation formation during storage of highly-concentrated antibody-containing formulations in a liquid condition by using aspartic acid or glutamic acid as a counter ion species to the buffer (for example, histidine buffer or tris(hydroxymethyl)aminomethane buffer) or as a counter ion species to the stabilizer (for example, arginine) in the formulations.

In the present invention, buffers that can be used instead of histidine buffer and in which aspartic acid or glutamic acid is used as a counter ion species include tris(hydroxymethyl)aminomethane (Tris) and imidazole. Such buffers can also be added to the histidine buffer of the present invention.

In the present invention, stabilizers to which aspartic acid or glutamic acid can be used as a counter ion species include argininamide, lysine, meglumine, spermine, spermidine, magnesium, calcium, sodium, and potassium, in addition to arginine.

As described above, the present invention provides stable antibody-containing formulations that comprise histidine-aspartate buffer or histidine-glutamate buffer, or tris(hydroxymethyl)aminomethane-aspartate buffer or tris(hydroxymethyl)aminomethane-glutamate buffer. A much higher stabilization effect is achieved in the antibody-containing formulations of the present invention when arginine-aspartate or arginine-glutamate is additionally contained. Thus, the present invention relates to antibody-containing formulations which contain a salt that combines a basic amino acid such as histidine or arginine (preferably, histidine and/or arginine) or tris(hydroxymethyl)aminomethane with aspartic acid or glutamic acid in liquid.

The histidine used in the present invention may be histidine itself or a derivative thereof, and L-histidine is particularly preferred. The arginine used in the present invention may be arginine itself, a derivative thereof, or a salt thereof, and L-arginine or a salt thereof is particularly preferable. Preferred salts of arginine include aspartate salt and glutamate salt.

In the formulations of the present invention, the concentration (amount) of histidine-aspartate buffer or histidine-glutamate buffer is preferably 1 to 100 mM, more preferably 5 to 100 mM, even more preferably 5 to 50 mM, and still more preferably 10 to 25 mM.

In the formulations of the present invention, the concentration (amount) of arginine is preferably 5 to 300 mM, more preferably 25 to 200 mM, and still more preferably 50 to 150 mM.

The formulations of the present invention may be solutions (antibody-containing liquid formulations) or lyophilized formulations. The liquid formulations of the present invention also include solutions before lyophilization step(s), and the dissolved solutions. The liquid formulations of the present invention are preferably produced without the lyophilization step(s) in production. Meanwhile, the lyophilized formulations of the present invention can be obtained by lyophilizing the liquid formulations of the present invention using methods known to those skilled in the art.

The pH of the formulations of the present invention is preferably 4 to 8, more preferably 5.0 to 7.5, and still more preferably 5.5 to 6.5.

The viscosity of the liquid formulations of the present invention at room temperature (25° C.) is preferably 30 mPa·s or less, more preferably 20 mPa·s or less, and still more preferably 15 mPa·s or less.

Significant changes are not observed for the liquid formulations of the present invention for at least 6 months, preferably 12 months, more preferably two years, even more preferably three years at refrigeration temperature (2° C. to 8° C.), or for at least six months, preferably one year, and more preferably two years at room temperature (22° C. to 28° C.). Specifically, the present invention relates to liquid formulations that are stable for at least six months at 22° C. to 28° C.

The liquid formulations of the present invention can be frozen and stored at a temperature within the range of −30° C. to −10° C.

The formulations of the present invention may additionally contain surfactants. As used in the present invention, preferred surfactants include polyoxyethylene sorbitan fatty acid esters and polyoxyethylene polyoxypropylene alkyl ethers, and more preferred surfactants include polysorbates 20 and 80, and Pluronic F-68 (poloxamer 188). The surfactants can be added to the formulations of the present invention in general at 0.0001% to 10% (w/v), preferably at 0.001% to 5%, and more preferably at 0.005% to 3%.

The formulations of the present invention may further contain amino acids. As used in the preset invention, preferred amino acids include natural amino acids and amino acid derivatives, and particularly preferred amino acids include L-methionine and L-proline.

The formulations of the present invention may further contain sugars. The preferred sugars used in the present invention include sucrose, trehalose, meglumine, and sorbitol.

The amount of amino acid or sugar that can be added to the formulations of the present invention is generally 1 to 1000 mM, preferably 5 to 500 mM, and more preferably 10 to 300 mM.

The formulations of the present invention may further contain inorganic salts. The preferred inorganic salts used in the present invention include magnesium salts and calcium salts.

The formulations of the present invention are substantially constituted by the ingredients of A to D below.
(A) anti-IL-6 receptor antibody;
(B) histidine-aspartate buffer and/or histidine-glutamate buffer;
(C) arginine (including arginine-aspartate and arginine-glutamate), amino acids other than arginine, and/or sugars as needed; and
(D) surfactants.

"Substantially constituted" means that the concentrations of the optional additives described below, which are ingredients other than the ingredients generally added to the formulations, are 5 mM or less, preferably 2 mM or less, and more preferably 1 mM or less. Such optional additives include cryoprotectants, suspending agents, solubilizing agents, isotonizing agents, preservatives, adsorption inhibitors, diluents, excipients, pH adjustors, analgesics, sulfur-containing reducing agents, and antioxidants.

Furthermore, it is preferred that the formulations of the present invention do not contain anions other than aspartic acid and glutamic acid, as counter ions to the buffer or stabilizer. In an embodiment, such formulations include, for example, those that do not substantially contain chloride ion and acetate ion. "Substantially do not contain chloride ion and acetate ion" means that the concentrations of chloride ion and acetate ion are, for example, 5 mM or less, preferably 2 mM or less, and more preferably 1 mM or less. Highly stable antibody-containing formulations can be produced without increasing the osmotic pressure, as a result of using aspartic acid and glutamic acid which have higher stabilizing effect as a counter ions and not substantially including chloride ion and acetate ion with poorer stabilization effect.

If needed, the formulations of the present invention may further contain appropriate cryoprotectants, suspending agents, solubilizing agents, isotonizing agents, preservatives, adsorption inhibitors, diluents, excipients, pH adjustors, analgesics, sulfur-containing reducing agents, antioxidants, and such.

Cryoprotectants include, for example, sugars such as trehalose, sucrose, and sorbitol.

Solubilizing agents include, for example, polyoxyethylene hydrogenated castor oil, polysorbate 80, nicotinamide, polyoxyethylene sorbitan monolaurate, macrogol, and castor oil fatty acid ethyl ester.

Isotonizing agents include, for example, sodium chloride, potassium chloride, and calcium chloride.

Preservatives include, for example, methyl parahydroxybenzoate, ethyl parahydroxybenzoate, sorbic acid, phenol, cresol, and chlorocresol.

Adsorption inhibitors include, for example, human serum albumin, lecithin, dextran, ethylene oxide/propylene oxide copolymer, hydroxypropyl cellulose, methyl cellulose, polyoxyethylene hydrogenated castor oil, and polyethylene glycol.

Sulfur-containing reducing agents include, for example, those containing sulfhydryl groups such as N-acetylcysteine, N-acetylhomocysteine, thioctic acid, thiodiglycol, thioethanol amine, thioglycerol, thiosorbitol, thioglycolic acid and salts thereof, sodium thiosulfate, glutathione, and thioalkanoic acids having one to seven carbon atoms.

Antioxidants include, for example, erythorbic acid, dibutylhydroxytoluene, butylhydroxyanisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

The formulations of the present invention may be administered orally or parenterally. In general, the formulations are administered parenterally, specifically via injection, transdermal administration, transmucosal administration, nasal administration, pulmonary administration, or the like. Injection includes, for example, systemic and local administrations by subcutaneous injection, intravenous injection, intramuscular injection, or such. The injection volume is limited in subcutaneous injection; however, a single antibody dose may be a large quantity (about 100 to 200 mg). Thus, the formulations of the present invention are particularly suitable for subcutaneous administration (injection).

In terms of pain, it is preferred that the osmotic pressure ratio of buffering agent is close to isotonic 1.0 in formulations for subcutaneous administration. Thus, the osmotic pressure ratio of the liquid formulations of the present invention is preferably about 1. Arginine, sugars, and such are added to improve the stability of formulations during storage. However, when the osmotic pressure is greater than the isotonic level, it may cause pain of subcutaneous administration. Thus, adding such stabilizers with consideration of osmotic pressure is preferred.

Furthermore, the present invention relates to use of basic amino acid-aspartate or basic amino acid-glutamate in manufacturing a stable antibody-comprising formulation; and aspartic acid or glutamic acid as a counter ion species to a buffer or stabilizer in a highly-concentrated antibody-comprising formulation, used in a method for suppressing aggregation during frozen storage or liquid storage of the formulation.

All prior-art documents cited in the specification are incorporated herein by reference.

EXAMPLES

Hereinbelow, the present invention is specifically described with reference to the Examples, but the scope of the present invention is not to be construed as being limited thereto.

[Example 1] Assessment of the Stabilization Effect of Counter Ion Species Using Mab1 and Mab2

Mab1 (H chain/SEQ ID NO: 1; L chain/SEQ ID NO: 2) and Mab2 (H chain/SEQ ID NO: 3; L chain/SEQ ID NO: 4;

tocilizumab), which are described as an anti-IL-6 receptor antibody in WO 2009/041621, were expressed by a method known to those skilled in the art using a stable expression CHO cell line, and then purified to high purity by a method known to those skilled in the art using protein A. Purified Mab1 and Mab2 were used in the stability study described in the Examples below.

The stability of two types of formulations, containing histidine-chloride or histidine-acetate, was assessed by freeze-thawing or by storage at 40° C. using Mab1 and Mab2. Mab1 and Mab2 formulations were prepared by overnight dialysis against each formulated solution (Table 1), followed by concentration of the solutions. The final concentrations of Mab1 and Mab2 were adjusted to 37 mg/ml. The freeze-thawing study was carried out by conducting ten cycles of slow freeze-thawing (freezing at −20° C. followed by thawing at room temperature), and then ten cycles of rapid freeze-thawing (freezing at −20° C. followed by thawing in warm water bath (37° C.)). The amount of aggregate in each formulation after freeze-thawing or storage at 40° C. was calculated by the area percentage method using size exclusion chromatography (SEC). An increase of the aggregates (%) suggests reduced stability of Mab1 or Mab2. Thus, increase in the amount of aggregate was used as an indicator to compare the stability between respective formulations.

Size Exclusion Chromatography (SEC)

Size exclusion chromatography (SEC) was performed to analyze the quantity of aggregates and low-molecular-weight degradation products in each formulation. Each formulation was diluted to about 0.4-2.0 mg/ml with the mobile phase described below, and then analyzed using G3000SW$_{XL}$ column (Tosoh Co.) at a flow rate of 0.5 ml/min with a mobile phase of 50 mM phosphate buffer (pH 7.0) containing 300 mM NaCl (detection wavelength: 220 nm). The elution peak that appeared earlier than the monomer peak was analyzed as the aggregates, and the elution peak that appeared after the monomer peak but earlier than the buffer-derived peak was analyzed as the low-molecular-weight degradation products. The respective contents (%) were calculated by the area percentage method.

TABLE 1

Formulation list

| No. | Buffer | Stabilizer | pH |
|---|---|---|---|
| 1 | 20 mM Histidine-Chloride | 150 mM NaCl | 6.0 |
| 2 | 20 mM Histidine-Acetate | | |

Figure 2:
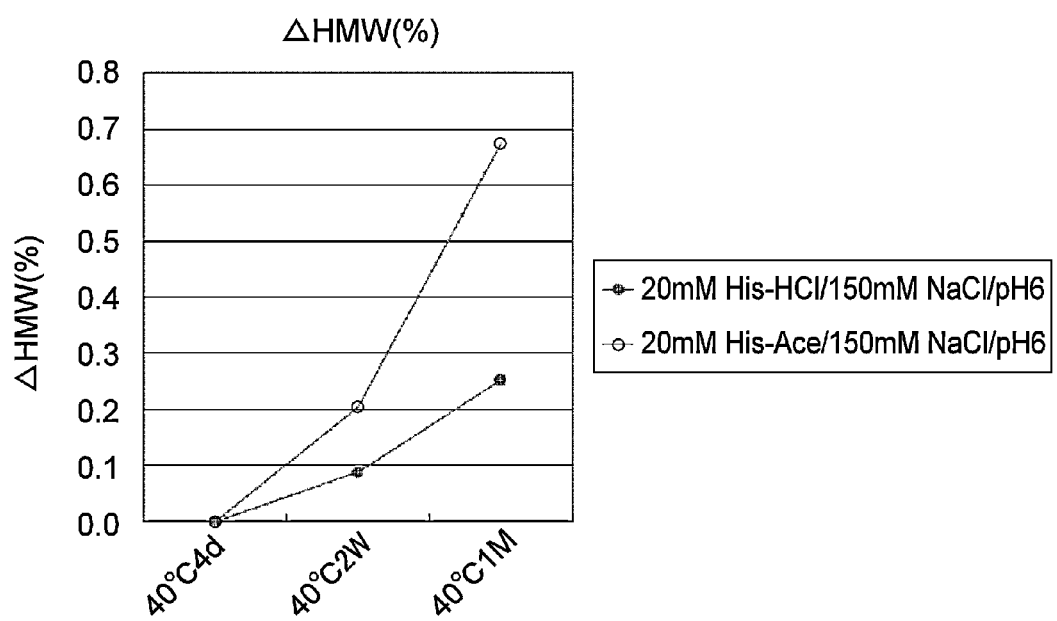
FIG. 2 is a graph plotted with time-dependent changes of the amount (%) of aggregate during storage of Mab2 at 40° C. on the vertical axis.
Figure 3:
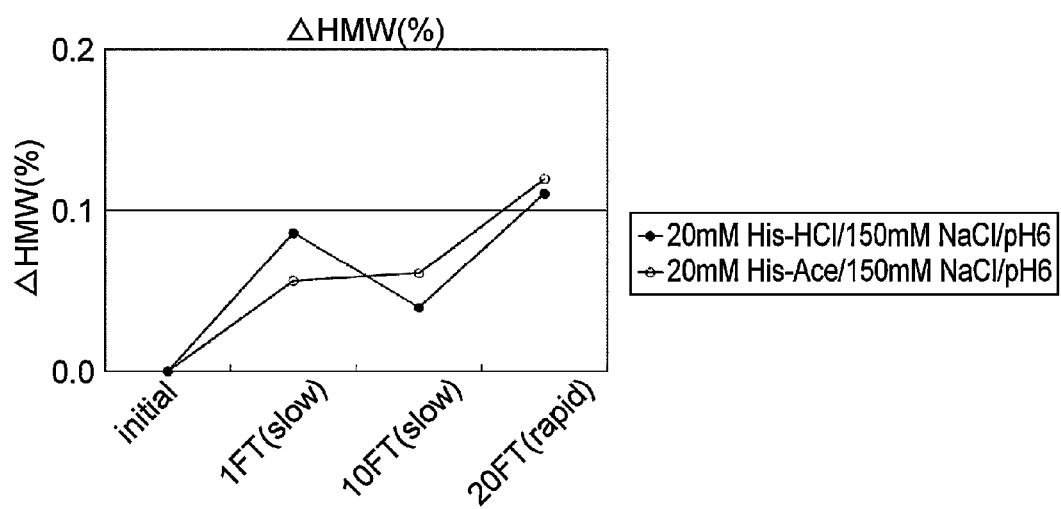
FIG. 3 is a graph plotted with time-dependent changes of the amount (%) of aggregate during freeze-thawing of Mab1 on the vertical axis.
Figure 4:
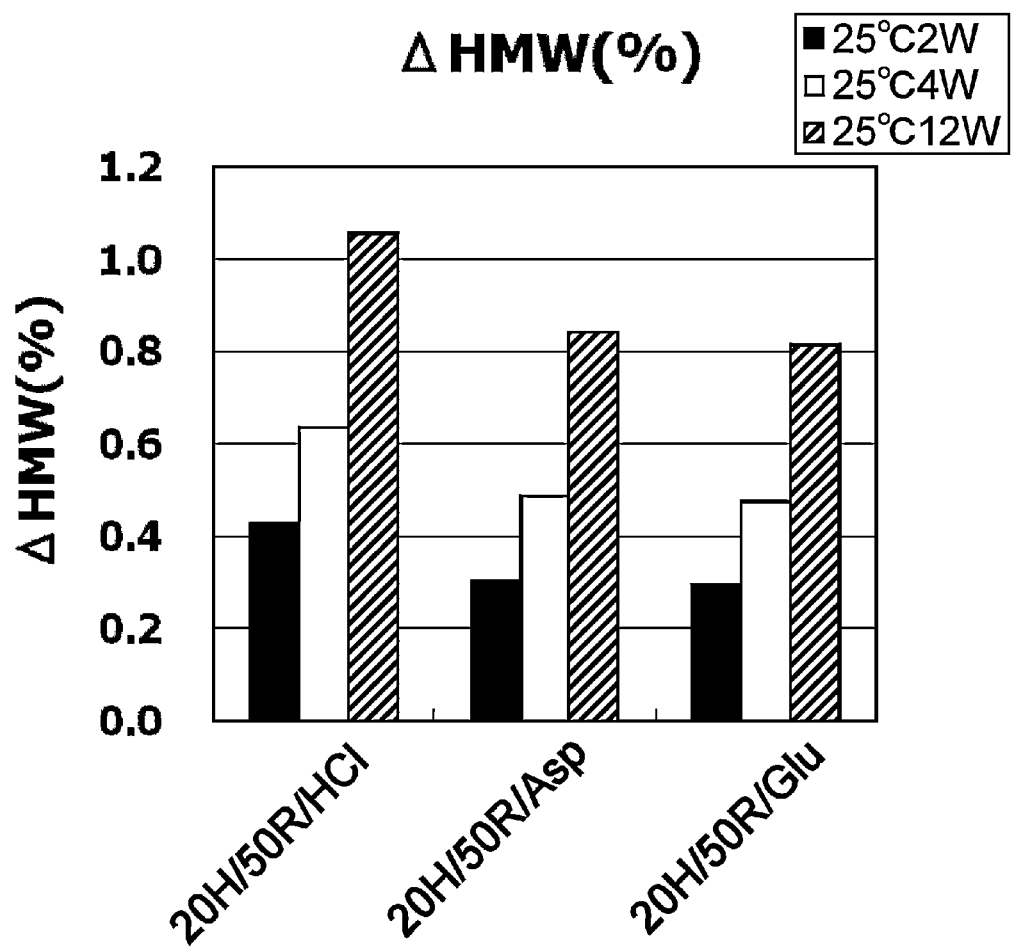
FIG. 4 is a graph plotted with time-dependent changes of the amount (%) of aggregate during storage of Mab1 at 25° C. on the vertical axis.
Figure 5:
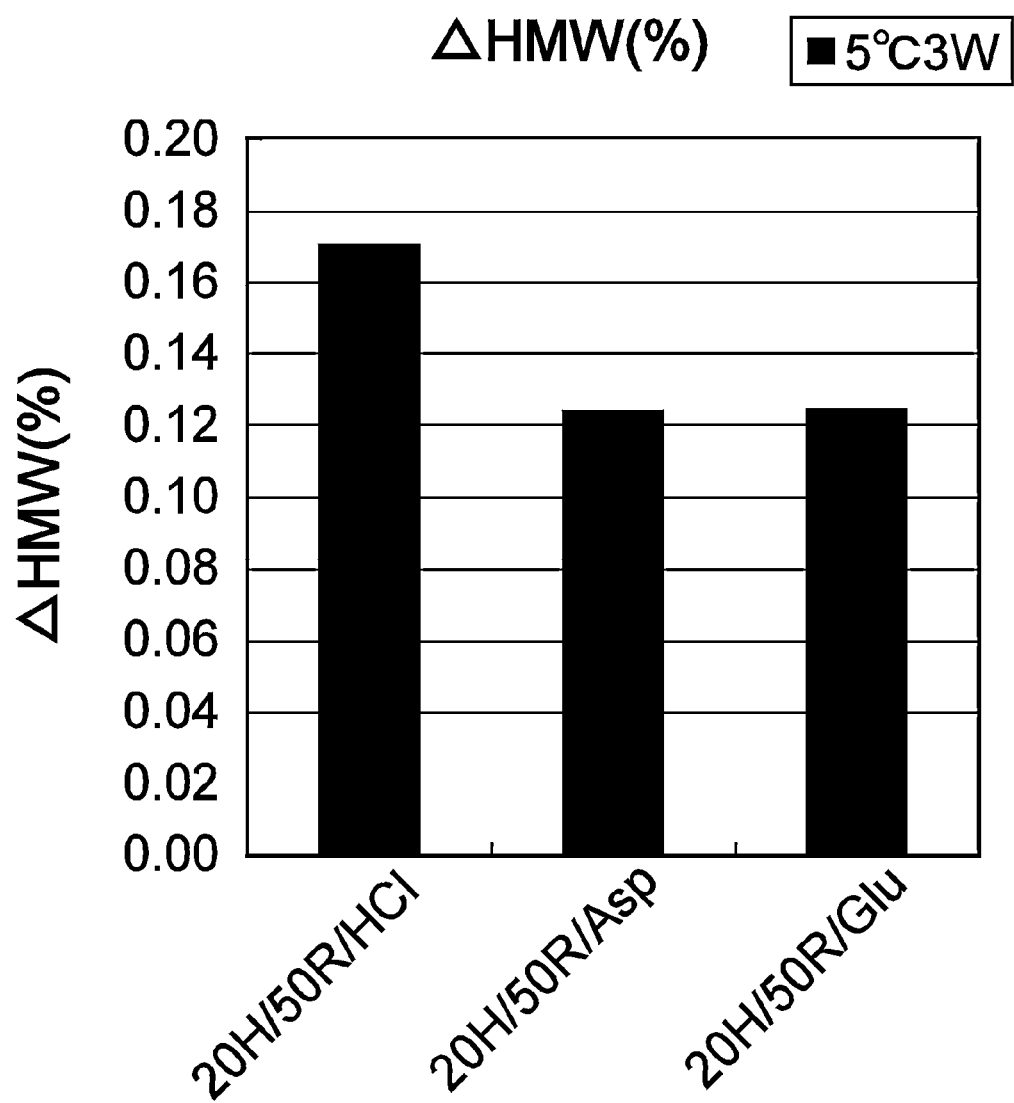
FIG. 5 is a graph plotted with time-dependent changes of the amount (%) of aggregate during storage of Mab1 at 5° C. on the vertical axis.
Figure 6:
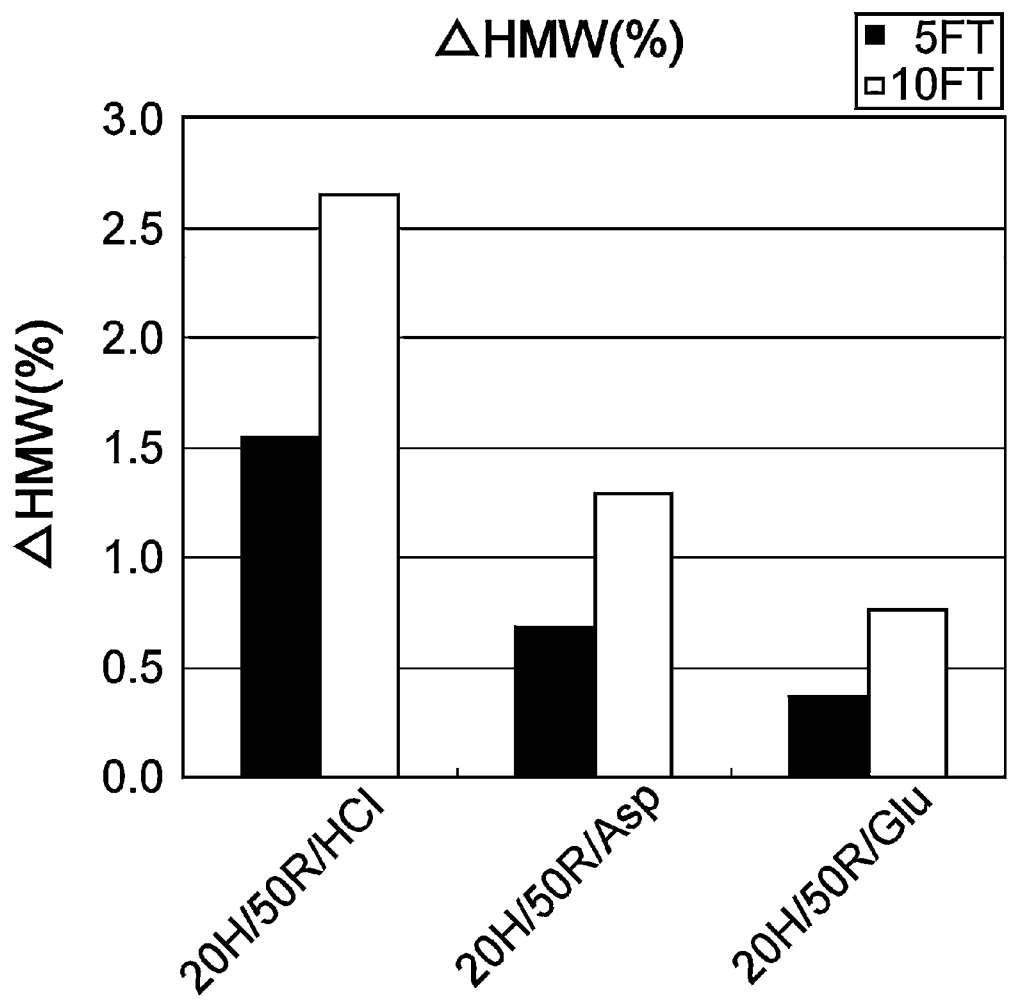
FIG. 6 is a graph plotted with time-dependent changes of the amount (%) of aggregate during freeze-thawing (−20° C. to room temperature) of Mab1 on the vertical axis.
Figure 7:
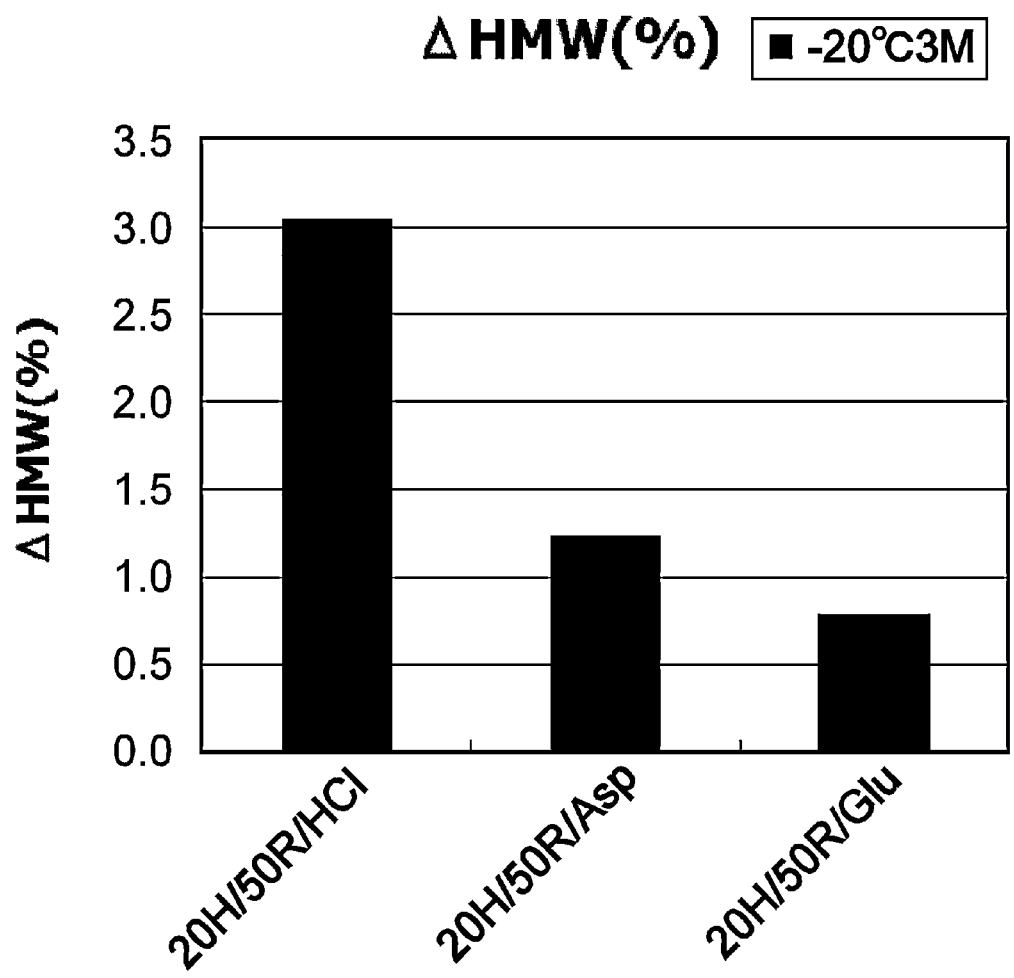
FIG. 7 is a graph plotted with the amount (%) of aggregate after three months of storage of Mab1 at −20° C. on the vertical axis.

The stability study results of the two types of formulations containing histidine-chloride or histidine-acetate using Mab1 and Mab2 are shown in FIGS. 1 to 3. The results demonstrated that Mab1 was slightly more stable in histidine-chloride than in histidine-acetate during both liquid storage and freeze-thawing. The result of liquid storage showed that Mab2 was about twofold more stable in histidine-chloride than in histidine-acetate.

[Example 2] Assessment of the Stabilization Effect of Counter Ion Species Using Mab1 (1)

In general, hydrochloric acid has been used as a counter ion species to histidine and arginine. According to a previous report (PCT/US2005/037471), results of assessing acetic acid, phosphoric acid, and sulfuric acid as a counter ion species to histidine showed that acetic acid has a superior stabilizing effect when used as a counter ion species to histidine. However, as described in Example 1 above, the present invention demonstrated that hydrochloric acid was slightly more superior than acetic acid as a counter anion species to histidine when used for Mab1 and Mab2. Hydrochloric acid is a common counter anion species, while hydrochloric acid has been reported to have a tendency of corroding stainless steel which is generally used for containers (Dent. Mater. 17:409-414 (2001); J. Pharm. Sci. 86:1250-1255 (1997)). Besides, it has been reported that the pH tends to alter in acetic acid because of its volatility (Injectable Drug Development, Authors: Pramod K. Gupta (Editor), Gayle A. Brazeau, Gayle A).

Thus, in this Example, the present inventors searched for involatile counter ions that are not corrosive for stainless steel and have a superior stabilization effect than acetic acid and hydrochloric acid, as a counter anion species in the buffer for Mab1 and Mab2. The present inventors assessed anion species other than hydrochloric acid, acetic acid, phosphoric acid, and sulfuric acid previously reported in PCT/US2005/037471. Specifically, aspartic acid and glutamic acid, which are both amino acids, were assessed as counter ion species. As described in Example 1, histidine-chloride was demonstrated to have a more superior stabilization effect than histidine-acetate in both Mab1 and Mab2, so the stabilization effect of counter ion species was compared to that of hydrochloric acid. Specifically, according to the three formulations shown in Table 2, the effect of hydrochloric acid, aspartic acid, and glutamic acid on stability were assessed as a counter anion species to histidine as a buffer or arginine as a stabilizer using Mab1.

Each formulation was prepared by the same method as described in Example 1. Mab1 was dialyzed against the solution of each formulation (Table 2) overnight. Then, each solution was concentrated, and the final concentration of Mab1 was adjusted to 200 mg/ml. The freeze-thawing study was carried out by conducting ten cycles of slow freeze-thawing (freezing at −20° C. followed by thawing at room temperature). The method for preparing each formulated solution is described below. Formulation No. 3 sample was prepared as follows: L-histidine and L-arginine were dissolved in MilliQ water at 20 mM and 50 mM, respectively, and the solutions were titrated to pH 6 with 1 N hydrochloric acid. Formulation Nos. 4 and 5 samples were prepared as follows: L-histidine, L-arginine, and L-aspartic acid or L-glutamic acid were dissolved in MilliQ water at 20 mM, 50 mM, and 60 mM, respectively, and then the solutions were titrated to pH 6 with a 30 to 40 mM L-aspartic acid or L-glutamic acid solution. The amount of aggregate in each sample after freeze-thawing or storage at −20° C., 25° C., and 5° C. was calculated by the area percentage method using size exclusion chromatography (SEC).

TABLE 2

Formulation list

| No. | Buffer | Stabilizer | pH |
|---|---|---|---|
| 3 | 20 mM Histidine-Chloride | 50 mM Arg-Chloride | 6.0 |
| 4 | 20 mM Histidine-Aspartate | 50 mM Arg-Aspartate | |
| 5 | 20 mM Histidine-Glutamate | 50 mM Arg-Glutamate | |

The increased amount (%) of aggregate during freeze-thawing or storage at −20° C., 25° C., and 5° C. for each formulation is shown in FIGS. 4 to 7. The increased amount (%) of aggregate during storage at 5° C. and 25° C., showed that stability was enhanced in the order of: glutamic acid=aspartic acid>hydrochloric acid as counter ion species to histidine and arginine. Thus, it was demonstrated that the stability of Mab1 was improved by using aspartic acid or glutamic acid as a counter ion species, instead of hydrochloric acid. The same tendency was seen in freeze-thawing and frozen storage. The increased amount (%) of aggregate during storage at −20° C. for three months with the glutamic acid formulation, aspartic acid formulation, or hydrochloric acid formulation was about 0.8%, 1.2%, or 3.0%, respectively. Thus, the stabilization effect of glutamic acid was slightly stronger than that of aspartic acid.

Examples 1 and 2 demonstrated that when used as a counter anion species, glutamic acid and aspartic acid have a superior Mab1-stabilizing effect than hydrochloric acid and acetic acid. There is no report demonstrating that glutamic acid and aspartic acid are volatile or corrosive for stainless steel. Thus, glutamic acid and aspartic acid are found to be promising as a counter anion species for Mab1. Specifically, histidine-glutamate and histidine-aspartate are superior as a buffer than histidine-chloride and histidine-acetate, and arginine-glutamate and arginine-aspartate are more superior as a stabilizer than arginine-chloride and arginine-acetate.

[Example 3] Assessment of the Stabilization Effect of Counter Ion Species Using Mab2 (1)

As described in Example 1, Mab2 was found to be more stable in histidine-chloride buffer than histidine-acetate buffer (like Mab1, FIG. 2). Furthermore, as described in Example 2, the stability in liquid and frozen conditions of Mab1 was significantly improved when aspartic acid or glutamic acid was used instead of hydrochloric acid as a counter ion species to histidine and arginine. In particular, the stability in frozen conditions of Mab1 was greatly improved (to about threefold) when glutamic acid was used instead of hydrochloric acid as a counter ion species to histidine and arginine. In this context, glutamic acid and hydrochloric acid were assessed as a counter ion species to histidine for their ability to stabilize Mab2 during freeze-thawing. Arginine-containing formulations which have high stabilization effect were also assessed at the same time, and used as a control to compare the stabilization effect observed when glutamic acid was used as a counter ion species to histidine.

Each formulation was prepared by the same method as described in Example 1. Mab2 was dialyzed overnight against each formulated solution (Table 3). Then, each solution was concentrated, and the final concentration of Mab2 was adjusted to about 40 to 230 mg/ml. The method for preparing the each formulated solution is described below. Formulation Nos. 6 and 8 samples were prepared as follows: L-histidine and L-arginine (formulation No. 8 alone) were each dissolved in MilliQ water at 50 mM, and the solutions were titrated to pH 6 with 1 N hydrochloric acid. Formulation No. 7 sample was prepared as follows: L-histidine and L-glutamic acid were dissolved in MilliQ water at 50 mM and 25 mM, respectively, and then the solution was titrated to pH 6 with a 30 to 40 mM L-glutamic acid solution. The concentration of Mab2 in each formulation after sample preparation is shown in Table 4. The freeze-thawing study was carried out with ten cycles of freezing at −20° C. followed by thawing at room temperature (slow freeze-thawing). Following slow freeze-thawing, the amount of aggregate in each formulation was calculated by the area percentage method using size exclusion chromatography (SEC).

TABLE 3

Formulation list

| No. | Buffer | Stabilizer | pH |
|---|---|---|---|
| 6 | 50 mM Histidine-Chloride | — | 6.0 |
| 7 | 50 mM Histidine-Glutamate | | |
| 8 | 50 mM Histidine-Chloride | 50 mM Arginine-Chloride | |

TABLE 4

Measurement result: List of Mab2 concentration in solution of each formulation

| No. | Buffer | Stabilizer | pH | Mab2 Concentration (mg/mL) |
|---|---|---|---|---|
| 6A | 50 mM Histidine-Chloride | — | 6.0 | 47 |
| 6B | | | | 70 |
| 6C | | | | 97 |
| 6D | | | | 122 |
| 6E | | | | 143 |
| 6F | | | | 164 |
| 6G | | | | 186 |
| 6H | | | | 229 |
| 7A | 50 mM Histidine-Glutamate | | | 46 |
| 7B | | | | 72 |
| 7C | | | | 97 |
| 7D | | | | 119 |
| 7E | | | | 144 |
| 7F | | | | 165 |
| 7G | | | | 196 |
| 8A | 50 mM Histidine-Chloride | 50 mM Arginine-Chloride | | 44 |
| 8B | | | | 68 |
| 8C | | | | 94 |
| 8D | | | | 120 |
| 8E | | | | 144 |
| 8F | | | | 168 |
| 8G | | | | 192 |

Figure 8:
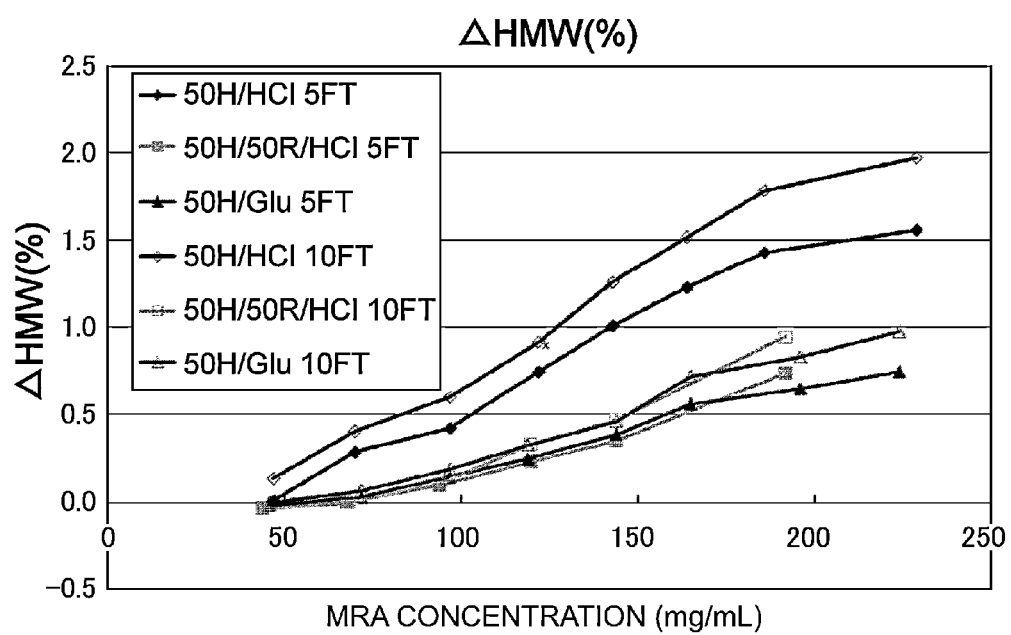
FIG. 8 is a graph plotted with time-dependent changes of the amount (%) of aggregate during freeze-thawing (−20° C. to room temperature) of Mab2 on the vertical axis.

The increased amount (%) of aggregate for each formulation in the freeze-thawing study is shown in FIG. 8. The results demonstrated that by using glutamic acid instead of hydrochloric acid as a counter ion species to histidine, the stability of Mab2 was improved to about two times. In addition, the stabilization effect of glutamic acid was comparable to that of 50 mM arginine chloride, which is a conventional stabilizer. Thus, glutamic acid alone was demonstrated to exert high stabilization effect as a counter ion species.

Meanwhile, it is believed that the osmotic pressure ratio of the buffer is preferably close to isotonic 1.0 in formulations for subcutaneous administration because of the injection pain. The stability during freeze-thawing was comparable between 50 mM histidine-chloride/50 mM arginine-chloride and 50 mM histidine-glutamate. The osmotic pressure of the buffer in the latter was about 100 mOsm lower than in the former. Thus, as described above, when the stability is improved by using aspartic acid or glutamic acid as a counter ion species, stability can be enhanced alone without increasing the osmotic pressure. This can be a great advantage in developing formulations for subcutaneous administration.

Meanwhile, arginine, sugars, and such are added to improve the stability of formulations during storage. However, when the osmotic pressure is greater than the isotonic level, it may cause injection pain at subcutaneous administration. Thus, such stabilizers must be added by considering the osmotic pressure (Injectable Drug Development, Authors: Pramod K. Gupta (Editor), Gayle A. Brazeau, Gayle A; Challenges in the development of high protein concentration formulations, J Pharm Sci, 2004, 93(6), 1390-1402). When hydrochloric acid or acetic acid is added as a counter anion species to histidine or arginine, neither hydrochloric acid nor acetic acid has the effect of stabilizing Mab1. Thus, hydrochloric acid and acetic acid only produce the effect of increasing the osmotic pressure. Accordingly, from the viewpoint of osmotic pressure, the concentration of ion species that do not have the stabilization effect should be minimized in the formulations. Specifically, also from the viewpoint of osmotic pressure, absence of hydrochloric acid and acetic acid is preferred. Histidine-glutamate and histidine-aspartate are superior as a buffer than histidine-chloride and histidine-acetate; and arginine-glutamate and arginine-aspartate are superior as a stabilizer than arginine-chloride and arginine-acetate.

[Example 4] Assessment of the Stabilization Effect of Counter Ion Species Using Mab1 (2)

As described in Examples 2 and 3, by using glutamic acid as a counter ion species to histidine and arginine, the stability of Mab1 was significantly improved to about two to three folds, in particular during frozen storage. In this context, a storage stability study at −20° C. was conducted to assess the stability of Mab1 at −20° C. storage when glutamic acid was used as a counter ion species to histidine and arginine, and a sugar (trehalose) as a stabilizer. Liquid storage and freeze-thawing study were also carried out at the same time.

Each formulation was prepared as follows: Mab1 was dialyzed overnight against each formulated solution (Table 5); then, the solutions were concentrated, and the final concentration of Mab1 was adjusted to 200 mg/ml. The method for preparing each formulated solution is described below. L-Histidine, L-arginine, L-glutamic acid, and trehalose were dissolved in MilliQ water at 100 mM, 50 mM, 100 mM, and 0 to 150 mM, respectively, and then the solutions were titrated to pH 6 with 30 to 40 mM L-glutamic acid solution. The freeze-thawing study was carried out with ten cycles of freezing at −20° C. followed by thawing at room temperature (slow freeze-thawing). The amount of aggregate in each formulation after freeze-thawing or storage at −20° C. and 25° C. was calculated by the area percentage method using size exclusion chromatography (SEC).

TABLE 5

Formulation list

| No. | Buffer | Stabilizer | Sugar | pH |
|---|---|---|---|---|
| 9 | 100 mM | 50 mM | — | 6.0 |
| 10 | Histidine- | Arginine- | 50 mM Trehalose | |
| 11 | Glutamate | Glutamate | 100 mM Trehalose | |
| 12 | | | 150 mM Trehalose | |

Figure 9:
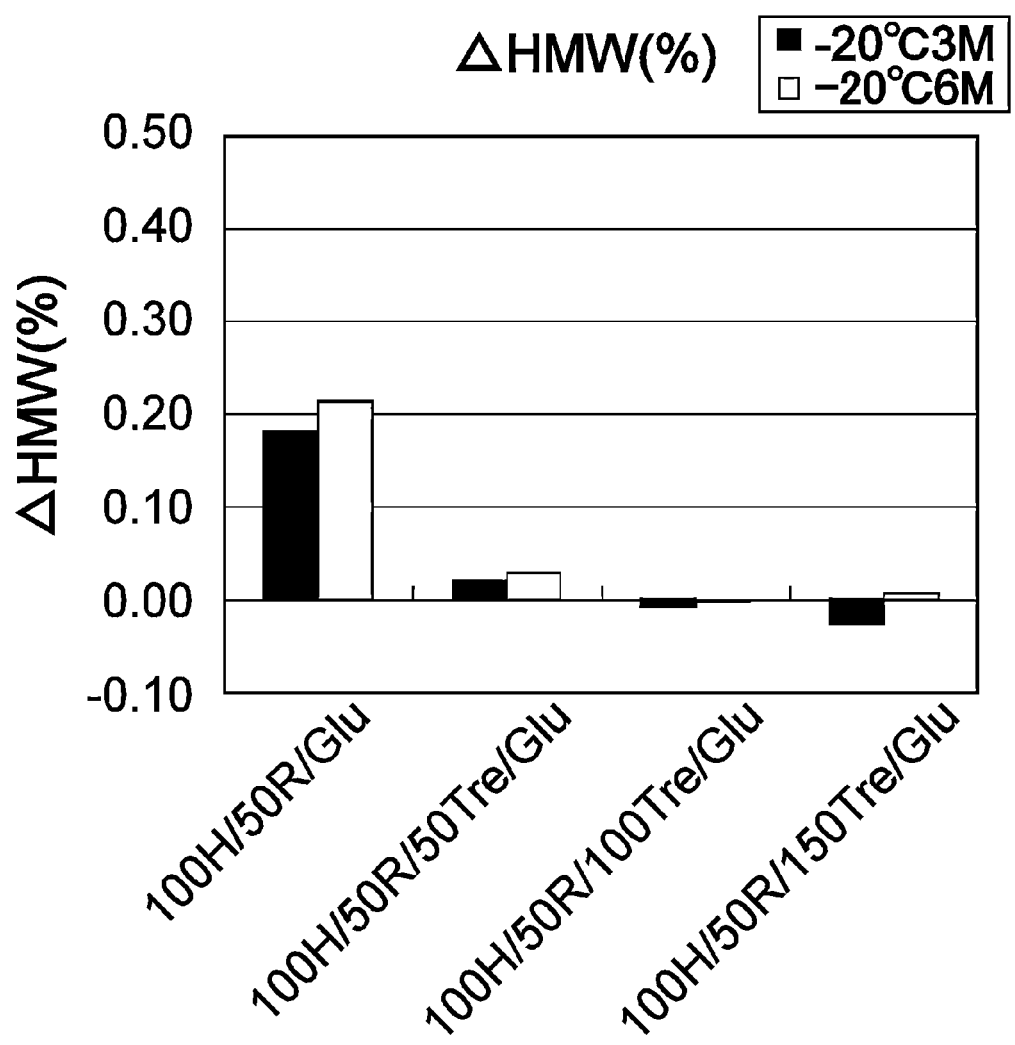
FIG. 9 is a graph plotted with the amount (%) of aggregate after storage of Mab1 at −20° C. on the vertical axis.
Figure 10:
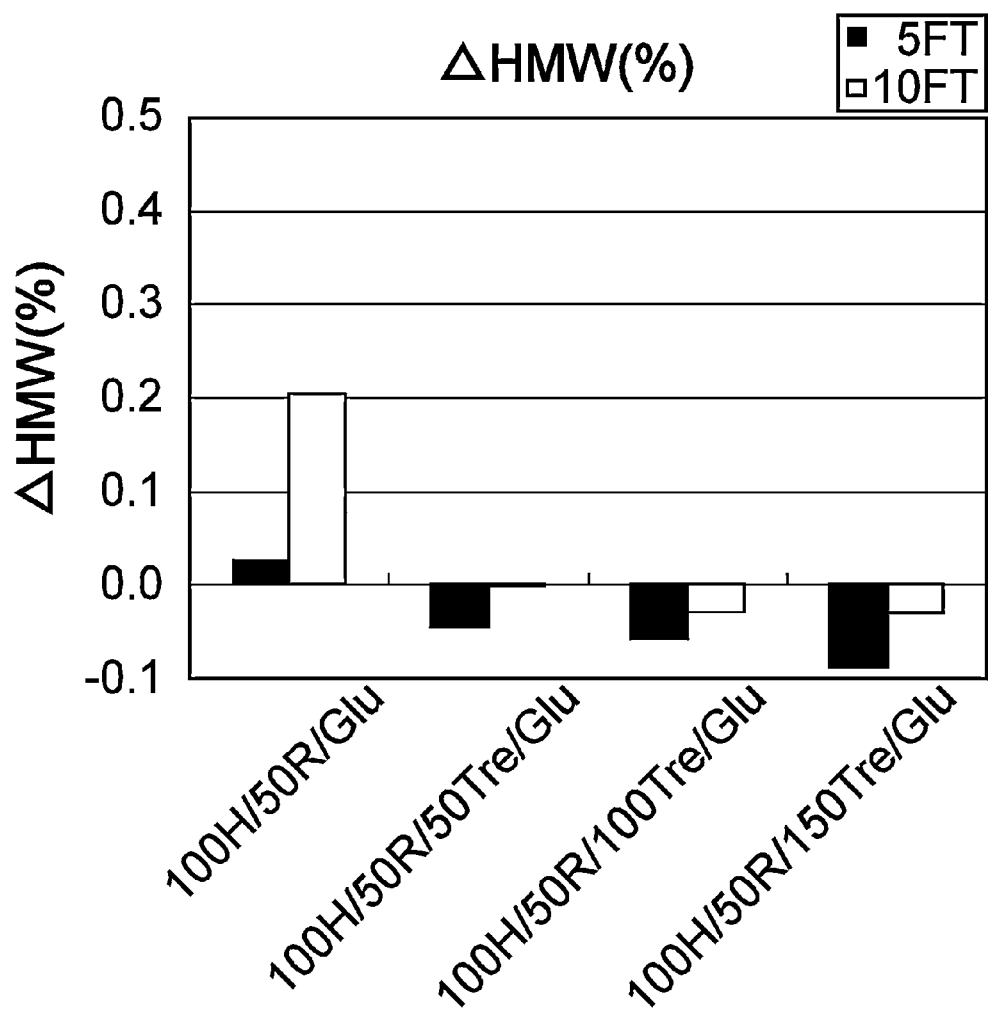
FIG. 10 is a graph plotted with the amount (%) of aggregate after freeze-thawing (−20° C. to room temperature) of Mab1 on the vertical axis.
Figure 11:
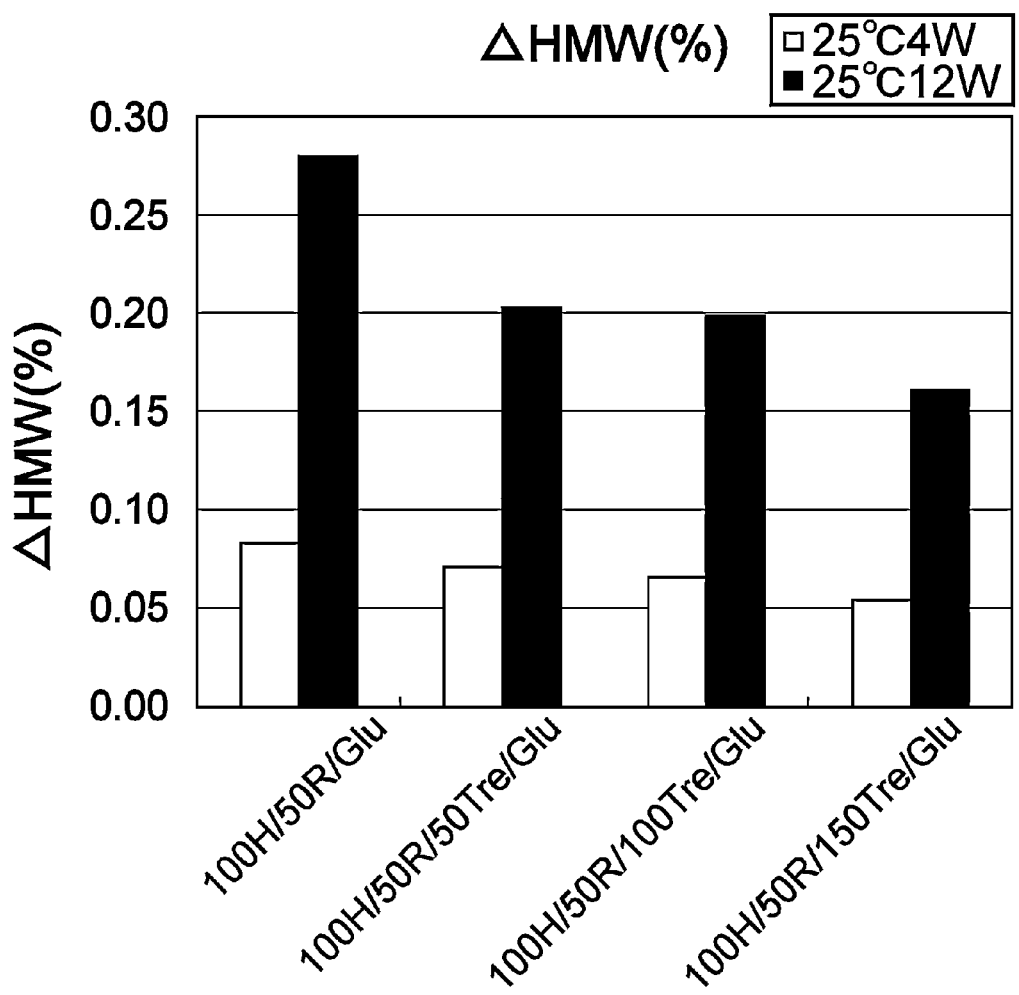
FIG. 11 is a graph plotted with the amount (%) of aggregate after three months of storage of Mab1 at 25° C. on the vertical axis.

The increased amount (%) of aggregate of each formulation after −20° C. storage, freeze-thawing, and 25° C. storage is shown in FIGS. 9 to 11. By adding 50 mM or more trehalose, a formulation with which the aggregate is hardly increased during storage at −20° C. and freeze-thawing was obtained, as seen from FIGS. 9 to 11. Furthermore, the trehalose concentration-dependent stabilization effect was observed in the liquid storage at 25° C. As described above, the present inventors discovered simple formulations consisting only of amino acids and sugar, which contribute to the stabilization during both liquid storage and frozen storage.

[Example 5] Assessment of the Stabilization Effect of Counter Ion Species Using Mab2 (2)

As described in Example 1, Mab2 was shown to be more stabilized by histidine-chloride than by histidine-acetate, like Mab1 (FIG. 2). Furthermore, as described in Example 2, the stability in liquid and in frozen conditions of Mab1 was significantly improved when aspartic acid or glutamic acid was used instead of hydrochloric acid as a counter ion species to histidine and arginine. In this context, the stability of Mab2 during liquid storage (25° C.) was used to assess hydrochloric acid and glutamic acid as a counter ion species to histidine. Arginine-containing formulations which have high stabilization effect were also assessed at the same time, and used as a control to compare the stabilization effect observed when glutamic acid is used as a counter ion species to histidine.

Each formulation was prepared by the same method as described in Example 1. Mab2 was dialyzed overnight against each formulated solution (Table 3). Then, the solutions were concentrated, and the final concentration of Mab2 was adjusted to about 40 to 230 mg/ml. The method for preparing the formulated solutions was the same as described in Example 3. The concentration of Mab2 in each formulation after sample preparation is shown in Table 4. The amount of aggregate in each formulation during two to four weeks of storage at 25° C. was calculated by the area percentage method using size exclusion chromatography (SEC).

Figure 12:
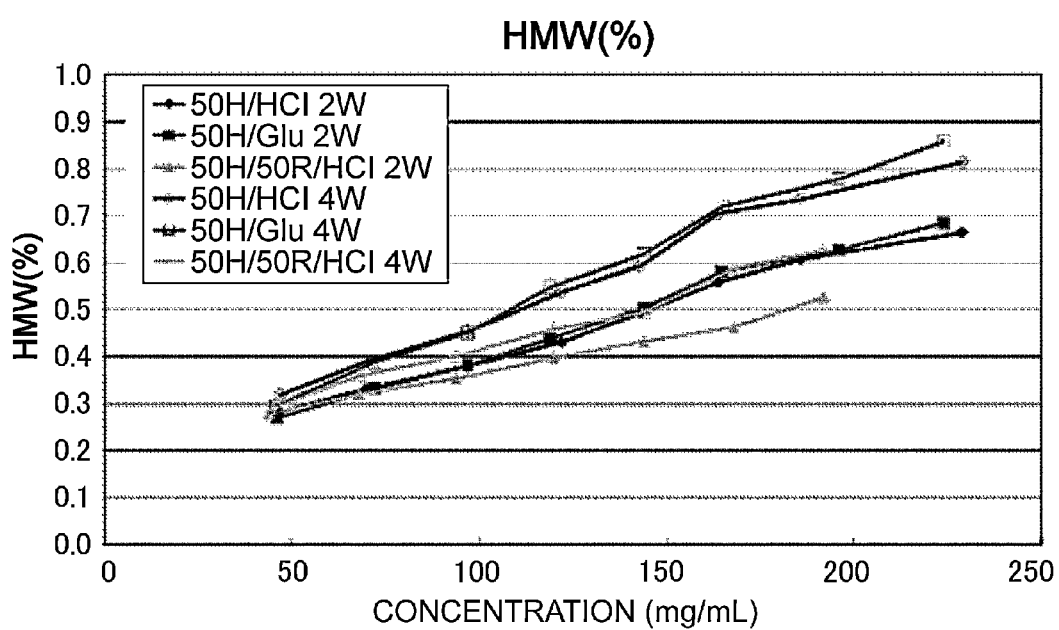
FIG. 12 is a graph plotted with time-dependent changes of the amount (%) of aggregate during storage of Mab2 at 25° C. on the vertical axis.
Figure 13:
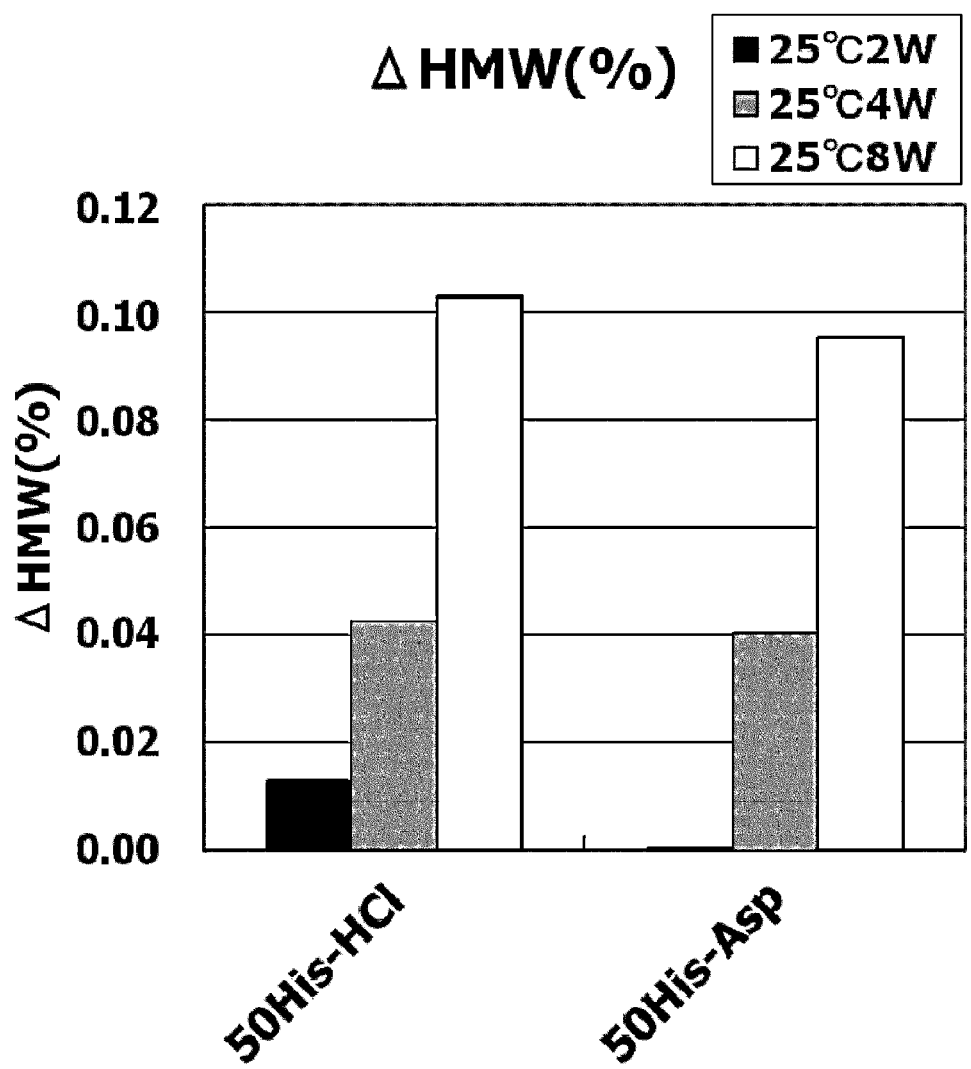
FIG. 13 is a graph plotted with time-dependent changes of the amount (%) of aggregate during storage of Mab3 at 25° C. on the vertical axis.
Figure 14:
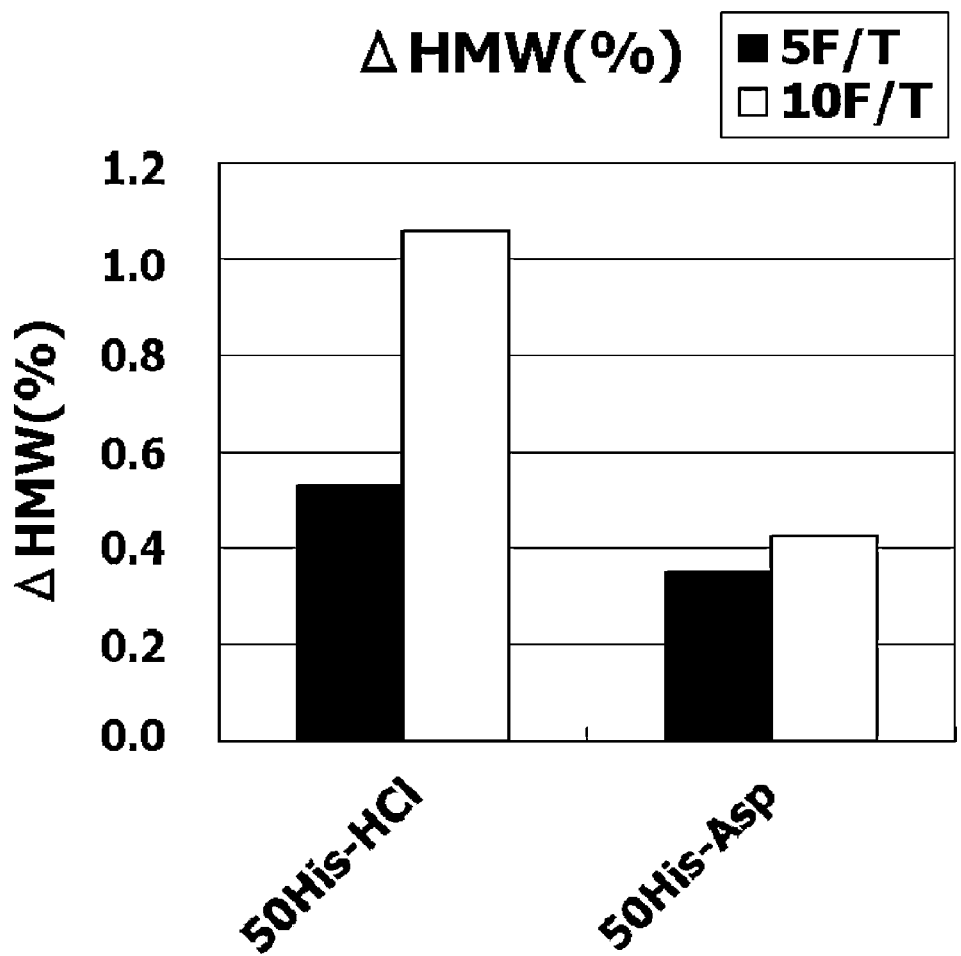
FIG. 14 is a graph plotted with time-dependent changes of the amount (%) of aggregate during freeze-thawing (between −20° C. and room temperature) of Mab3 on the vertical axis.
Figure 15:
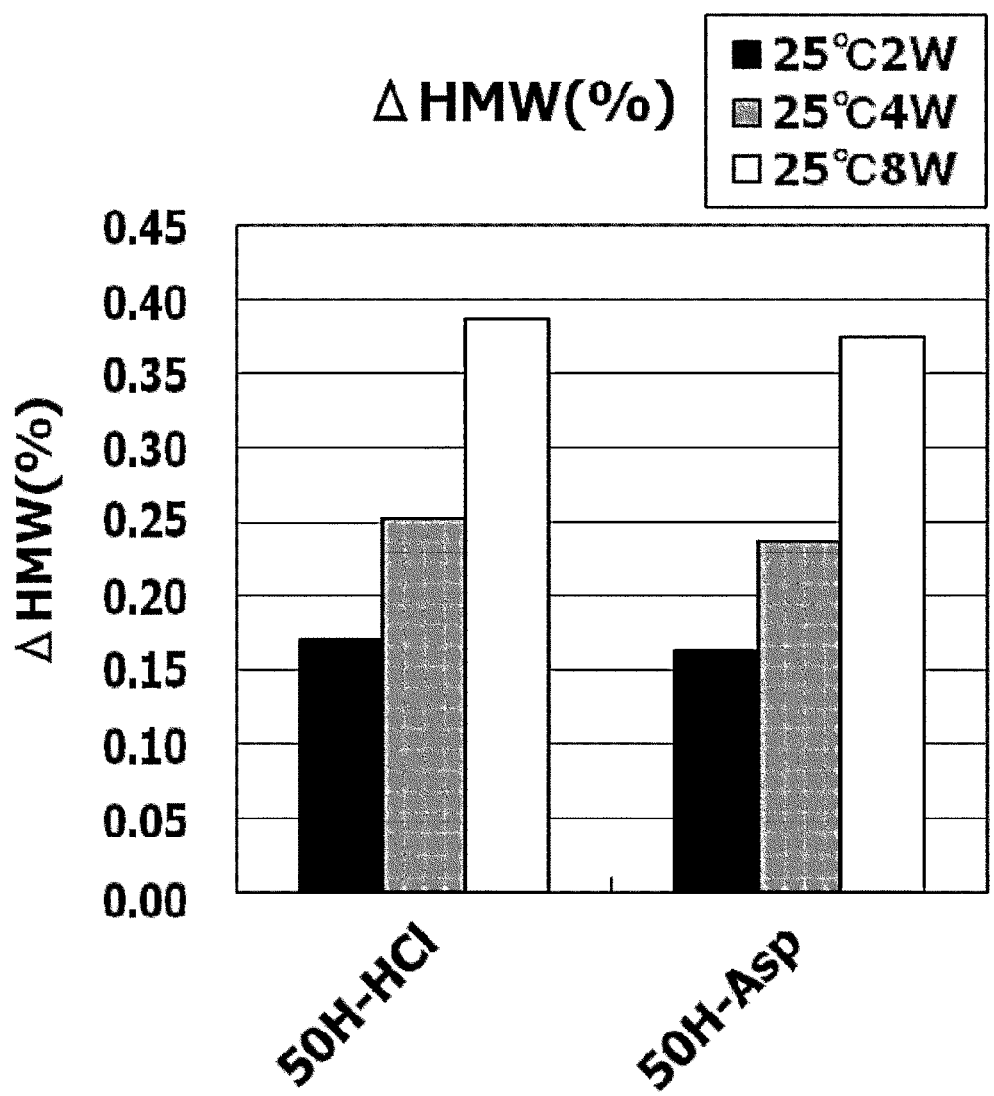
FIG. 15 is a graph plotted with time dependent changes of the amount (%) of aggregate during storage of Mab4 at 25° C. on the vertical axis.
Figure 16:
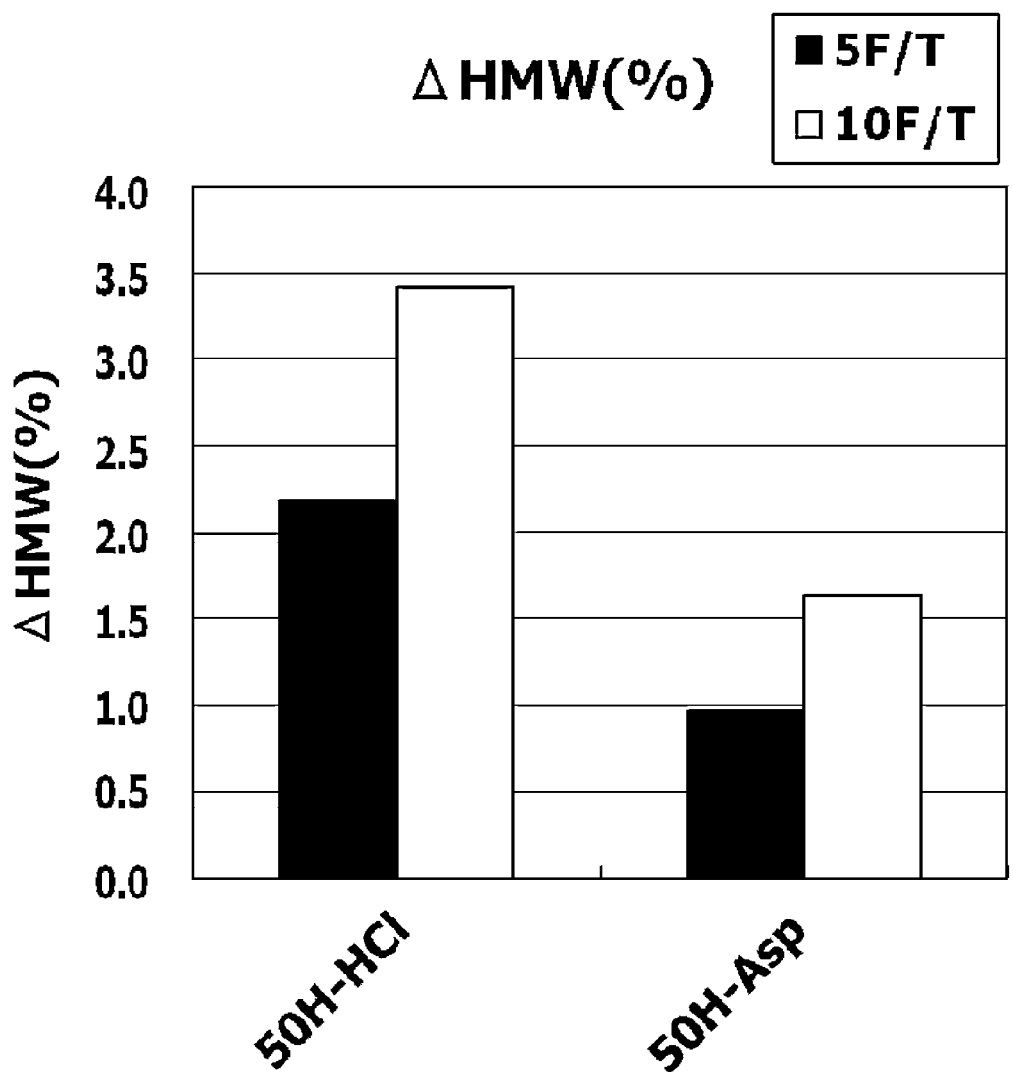
FIG. 16 is a graph plotted with time-dependent changes of the amount (%) of aggregate during freeze-thawing (between −20° C. and room temperature) of Mab4 on the vertical axis.
Figure 17:
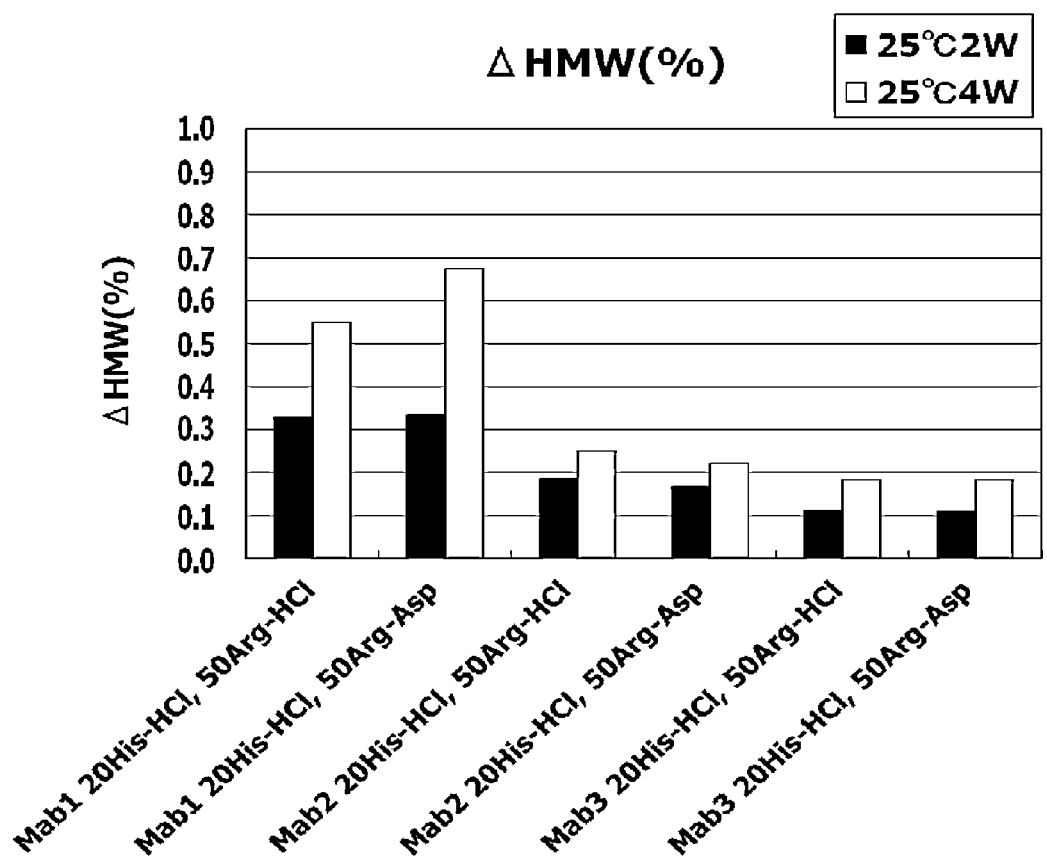
FIG. 17 is a graph plotted with time-dependent changes of the amount (%) of aggregate during storage of Mab1, Mab2, and Mab3 at 25° C. on the vertical axis.
Figure 18:
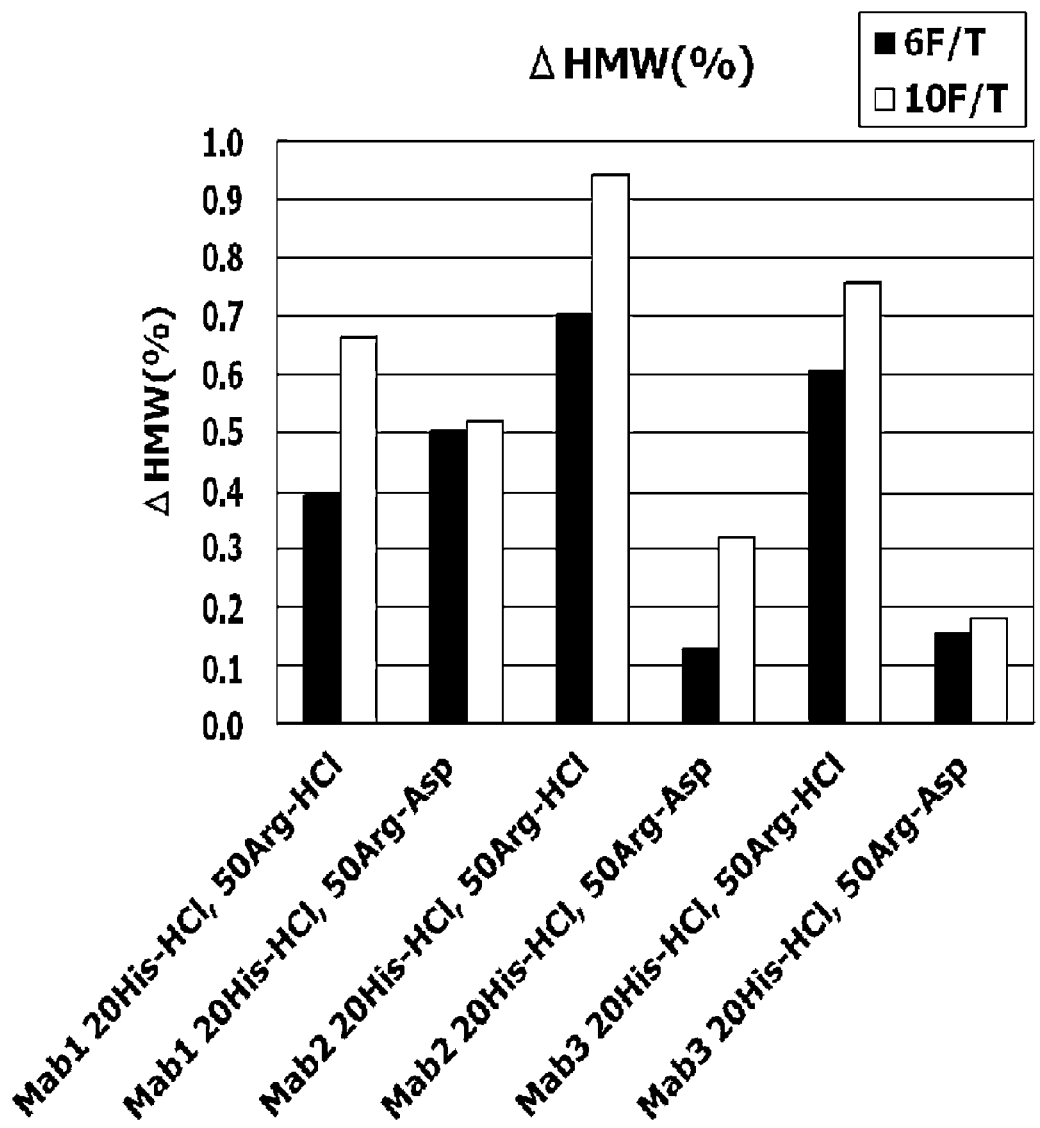
FIG. 18 is a graph plotted with time-dependent changes of the amount (%) of aggregate during freeze-thawing (between −20° C. and room temperature) of Mab1, Mab2, and Mab3 on the vertical axis.
Figure 19:
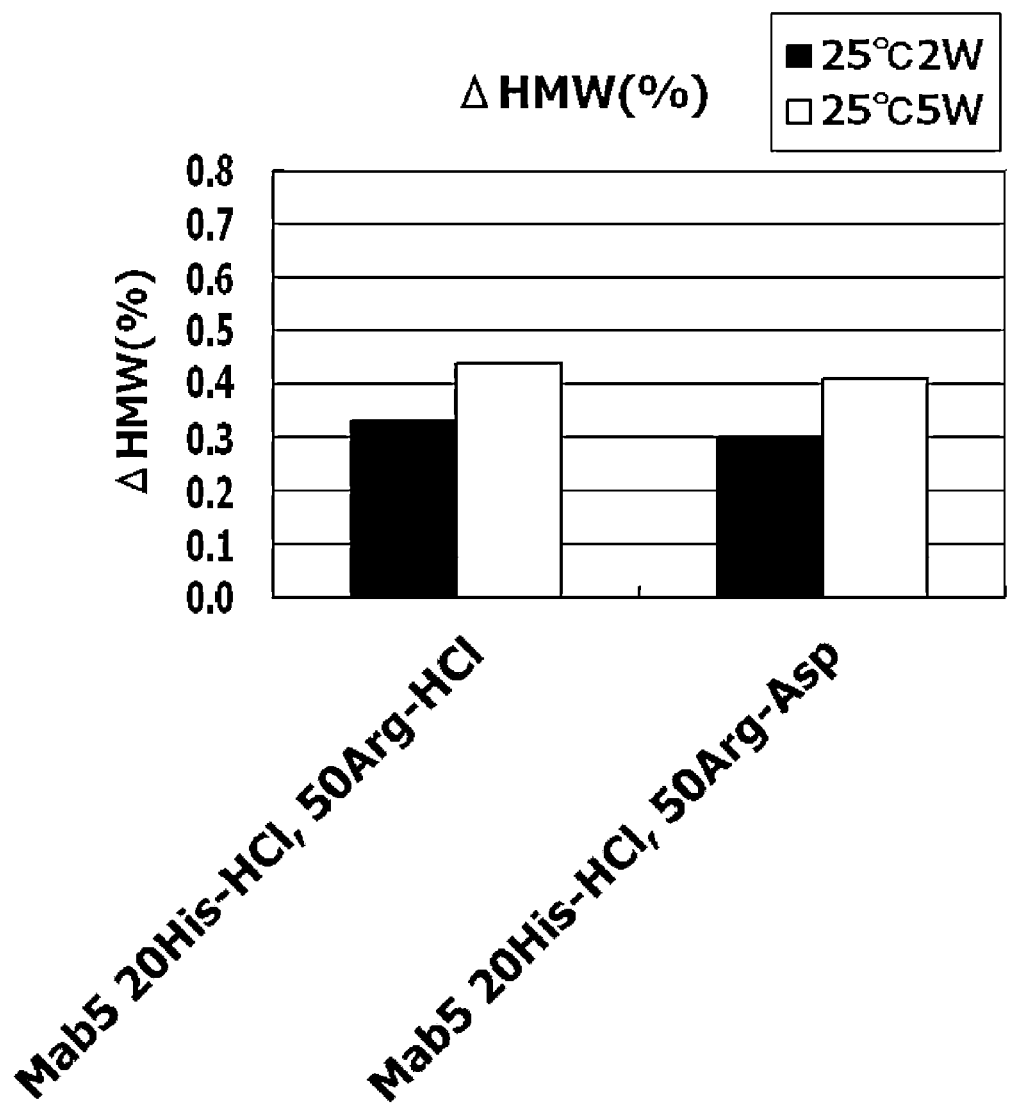
FIG. 19 is a graph plotted with time-dependent changes of the amount (%) of aggregate during storage of Mab5 at 25° C. on the vertical axis.
Figure 20:
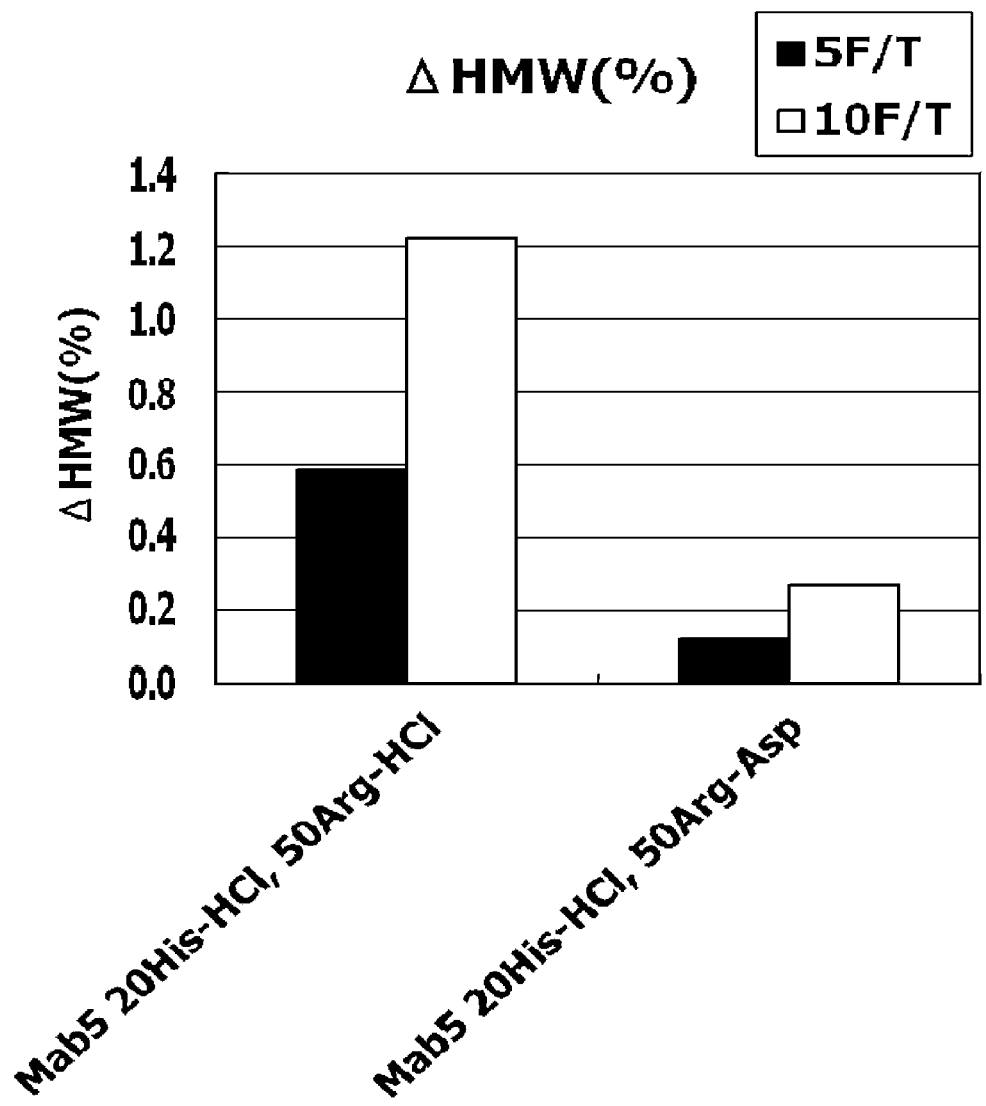
FIG. 20 is a graph plotted with time-dependent changes of the amount (%) of aggregate during freeze-thawing (between −20° C. and room temperature) of Mab5 on the vertical axis.

The increased amount (%) of aggregate for each formulation after storage at 25° C. is shown in FIG. 12. The results showed that, unlike in the freeze-thawing study, the stability of Mab2 was not altered even when glutamic acid was used instead of hydrochloric acid as a counter ion species to histidine. The pIs of Mab1 and Mab2 are 5.8 and 9.3, respectively. This suggests that the stabilization effect of counter ion species on antibodies with low pI in liquid storage was significant.

[Example 6] Assessment of Stabilization Effect of Counter Ion Species Using Mab1, Mab2, Mab3, Mab4, and Mab5

Mab3 is a bispecific antibody of factor IX and factor X and has an IgG4-derived constant region. Furthermore, its pI value has been lowered to 6.8 by altering the amino acid sequence.

Mab4 is a humanized anti-NR10 antibody (completely humanized NS22 antibody prepared according to the method described in Example 12 of WO 2009/072604), and its antibody class is IgG2. Its pI value has been lowered to 5.6 by altering the amino acid sequence.

Mab5 is a humanized anti-glypican 3 antibody (it was humanized by the method described in Example 24 of WO 2006/006693 and its L chain was altered by the method of Example 25). Its antibody class is IgG1.

As described in Examples 2 and 3, the stability in liquid and frozen conditions of Mab1 and Mab2 were demonstrated to be significantly improved when aspartic acid or glutamic acid was used instead of hydrochloric acid as a counter ion species to histidine and arginine. Then, Mab1 and Mab2 as well as Mab3, Mab4, and Mab5 which are antibodies modified to have an isoelectric point of 5 to 8 were used to assess the solution stability and freeze-thawing stability when hydrochloric acid and aspartic acid is used as a counter ion species to histidine and arginine. The pIs of Mab1, Mab2, Mab3, Mab4, and Mab5 are shown in Table 6 below.

TABLE 6

| Sample | Mab1 | Mab2 | Mab3 | Mab4 | Mab5 |
|---|---|---|---|---|---|
| pI | 5.8 | 9.4 | 6.8 | 5.6 | 9.0 |

Samples were prepared as follows: Mab1, Mab2, Mab3, Mab4, and Mab5 were dialyzed against each dialysis buffer (Table 7) overnight. Then, each antibody solution was concentrated, and a stock buffer for each formulation (Table 8) was added thereto so that the final antibody concentration was adjusted to about 100 to 190 mg/ml. A list of the formulated solutions prepared as described above is shown in Table 9. For each formulation, liquid storage study at 25° C. and freeze-thawing study were carried out. The freeze-thawing study was carried out in ten cycles of freezing at −20° C. followed by thawing at 25° C. (slow freeze-thawing). Following slow freeze-thawing, the amount of aggregate in each sample was calculated by the area percentage method using size exclusion chromatography (SEC).

TABLE 7

| No. | Sample | Dialysis buffer | pH |
|---|---|---|---|
| 13 | Mab3 | Water | 6.0 |
| 14 | Mab3 | | |
| 15 | Mab4 | 50 mM Histidine-Chloride | |
| 16 | Mab4 | 50 mM Histidine-Aspartate | |
| 17 | Mab2 | 20 mM Histidine-Chloride | |
| 18 | Mab2 | | |
| 19 | Mab1 | | |
| 20 | Mab1 | | |
| 21 | Mab3 | Water | |
| 22 | Mab3 | | |
| 23 | Mab5 | 20 mM Histidine-Chloride | |
| 24 | Mab5 | | |

TABLE 8

| No. | Sample | Stock buffer | pH |
|---|---|---|---|
| 13 | Mab3 | 500 mM Histidine-Chloride | 6.0 |
| 14 | Mab3 | 500 mM Histidine-Aspartate | |
| 15 | Mab4 | 50 mM Histidine-Chloride | |
| 16 | Mab4 | 50 mM Histidine-Aspartate | |
| 17 | Mab2 | 20 mM Histidine-Chloride, 500 mM Arginine-Chloride | |
| 18 | Mab2 | 20 mM Histidine-Chloride, 500 mM Arginine-Aspartate | |
| 19 | Mab1 | 20 mM Histidine-Chloride, 500 mM Arginine-Chloride | |
| 20 | Mab1 | 20 mM Histidine-Chloride, 500 mM Arginine-Aspartate | |
| 21 | Mab3 | 200 mM Histidine-Chloride, 500 mM Arginine-Chloride | |
| 22 | Mab3 | 200 mM Histidine-Chloride, 500 mM Arginine-Aspartate | |
| 23 | Mab5 | 20 mM Histidine-Chloride, 500 mM Arginine-Chloride | |
| 24 | Mab5 | 20 mM Histidine-Chloride, 500 mM Arginine-Aspartate | |

TABLE 9

| No. | Sample | formulation | pH | Mab concentration (mg/mL) |
|---|---|---|---|---|
| 13 | Mab3 | 50 mM Histidine-Chloride | 6.0 | 100 |
| 14 | Mab3 | 50 mM Histidine-Aspartate | | |
| 15 | Mab4 | 50 mM Histidine-Chloride | | |
| 16 | Mab4 | 50 mM Histidine-Aspartate | | |
| 17 | Mab2 | 20 mM Histidine-Chloride, 50 mM Arginine-Chloride | | 190 |
| 18 | Mab2 | 20 mM Histidine-Chloride, 50 mM Arginine-Aspartate | | |
| 19 | Mab1 | 20 mM Histidine-Chloride, 50 mM Arginine-Chloride | | 110 |
| 20 | Mab1 | 20 mM Histidine-Chloride, 50 mM Arginine-Aspartate | | |
| 21 | Mab3 | 20 mM Histidine-Chloride, 50 mM Arginine-Chloride | | |
| 22 | Mab3 | 20 mM Histidine-Chloride, 50 mM Arginine-Aspartate | | |
| 23 | Mab5 | 20 mM Histidine-Chloride, 50 mM Arginine-Chloride | | 120 |
| 24 | Mab5 | 20 mM Histidine-Chloride, 50 mM Arginine-Aspartate | | |

The result on the increased amount (%) of aggregate in each formulation after freeze-thawing or liquid storage at 25° C. is shown in FIGS. 13 to 20. Comparison of the increased amounts of aggregate during liquid storage at 25° C. demonstrated that the stability was comparable between the histidine-aspartate formulation and histidine-chloride formulation, and between the arginine-aspartate formulation and arginine-chloride formulation (FIGS. 13, 15, 17, and 19).

Meanwhile, comparison of the increased amounts of aggregate after freeze-thawing revealed that the stability with the histidine-aspartate formulation was two or more times higher than that with the histidine-chloride formulation, and the stability with the arginine-aspartate formulation was higher than that with the arginine-chloride formulation (FIGS. 14, 16, 18, and 20). Thus, the stability in frozen condition of antibody was demonstrated to be significantly improved by using aspartic acid instead of hydrochloric acid as a counter ion species to histidine or arginine.

[Example 7] Assessment of Stabilization Effect of Counter Ion Species Using Mab1, Mab2, Mab3, Mab4, and Mab5

As described in Examples 2, 3, and 6, the stability in liquid and frozen conditions of antibody was demonstrated to be significantly improved when aspartic acid or glutamic acid was used instead of hydrochloric acid as a counter ion species in the histidine formulation. Then, hydrochloric acid and aspartic acid were used as a counter ion species in the tris(hydroxymethyl) aminomethane (Tris) formulation, and assessed for the liquid storage stability and freeze-thawing stability using Mab4, Mab2, Mab3, Mab4, and Mab5.

Samples were prepared as follows: Mab1, Mab2, Mab3, Mab4, and Mab5 were dialyzed against each dialysis buffer (Table 10) overnight. Then, each antibody solution was concentrated, and a stock buffer for each formulation (Table 11) was added thereto so that the final antibody concentration was adjusted to about 100 to 110 mg/ml. A list of the formulated solutions prepared as described above is shown in Table 12. For each formulated solution, storage study at 25° C. and freeze-thawing study were carried out. The freeze-thawing study was carried out in ten cycles of freezing at −20° C. followed by thawing at 25° C. (slow freeze-thawing). Following slow freeze-thawing, the amount of aggregate in each sample was calculated by the area percentage method using size exclusion chromatography (SEC).

TABLE 10

| No. | Sample | Dialysis buffer | pH |
|---|---|---|---|
| 25 | Mab1 | 20 mM Tris-Chloride | 6.5 |
| 26 | Mab1 | 20 mM Tris-Aspartate | |
| 27 | Mab2 | 20 mM Tris-Chloride | |
| 28 | Mab2 | 20 mM Tris-Aspartate | |
| 29 | Mab3 | Water | |
| 30 | Mab3 | Water | |
| 31 | Mab4 | 20 mM Tris-Chloride | |
| 32 | Mab4 | 20 mM Tris-Aspartate | |
| 33 | Mab5 | 20 mM Tris-Chloride | |
| 34 | Mab5 | 20 mM Tris-Aspartate | |

TABLE 11

| No. | Sample | Stock buffer | pH |
|---|---|---|---|
| 25 | Mab1 | 20 mM Tris-Chloride, 500 mM Arginine-Chloride | 6.5 |
| 26 | Mab1 | 20 mM Tris-Chloride, 500 mM Arginine-Aspartate | |
| 27 | Mab2 | 20 mM Tris-Chloride, 500 mM Arginine-Chloride | |
| 28 | Mab2 | 20 mM Tris-Chloride, 500 mM Arginine-Aspartate | |
| 29 | Mab3 | 200 mM Tris-Chloride, 500 mM Arginine-Chloride | |
| 30 | Mab3 | 200 mM Tris-Chloride, 500 mM Arginine-Aspartate | |
| 31 | Mab4 | 20 mM Tris-Chloride, 500 mM Arginine-Chloride | |
| 32 | Mab4 | 20 mM Tris-Chloride, 500 mM Arginine-Aspartate | |
| 33 | Mab5 | 20 mM Tris-Chloride, 500 mM Arginine-Chloride | |
| 34 | Mab5 | 20 mM Tris-Chloride, 500 mM Arginine-Aspartate | |

TABLE 12

| No. | Sample | formulation | pH | Mab concentration (mg/mL) |
|---|---|---|---|---|
| 25 | Mab1 | 20 mM Tris-Chloride, 50 mM Arginine-Chloride | 6.5 | 100 |
| 26 | Mab1 | 20 mM Tris-Chloride, 50 mM Arginine-Aspartate | | |
| 27 | Mab2 | 20 mM Tris-Chloride, 50 mM Arginine-Chloride | | |
| 28 | Mab2 | 20 mM Tris-Chloride, 50 mM Arginine-Aspartate | | |
| 29 | Mab3 | 20 mM Tris-Chloride, 50 mM Arginine-Chloride | | |
| 30 | Mab3 | 20 mM Tris-Chloride, 50 mM Arginine-Aspartate | | |
| 31 | Mab4 | 20 mM Tris-Chloride, 50 mM Arginine-Chloride | | 110 |
| 32 | Mab4 | 20 mM Tris-Chloride, 50 mM Arginine-Aspartate | | |
| 33 | Mab5 | 20 mM Tris-Chloride, 50 mM Arginine-Chloride | | |
| 34 | Mab5 | 20 mM Tris-Chloride, 50 mM Arginine-Aspartate | | |

Figure 21:
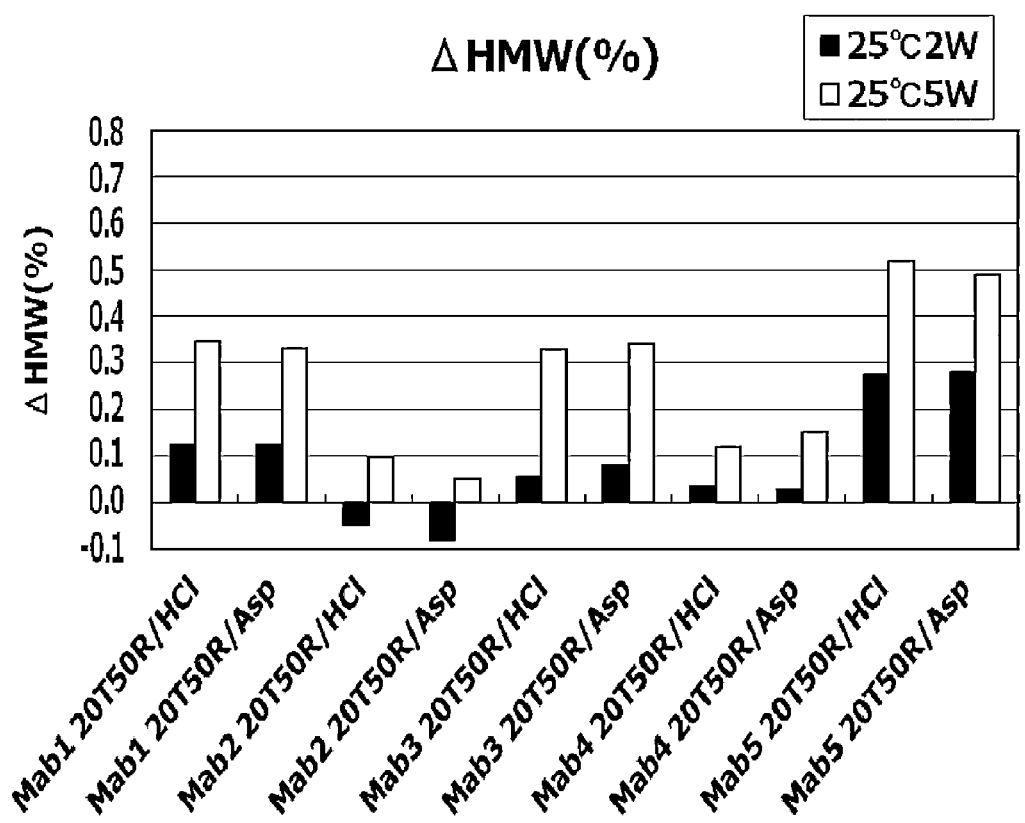
FIG. 21 is a graph plotted with time-dependent changes of the amount (%) of aggregate during storage of Mab1, Mab2, Mab3, Mab4, and Mab5 at 25° C. on the vertical axis.
Figure 22:
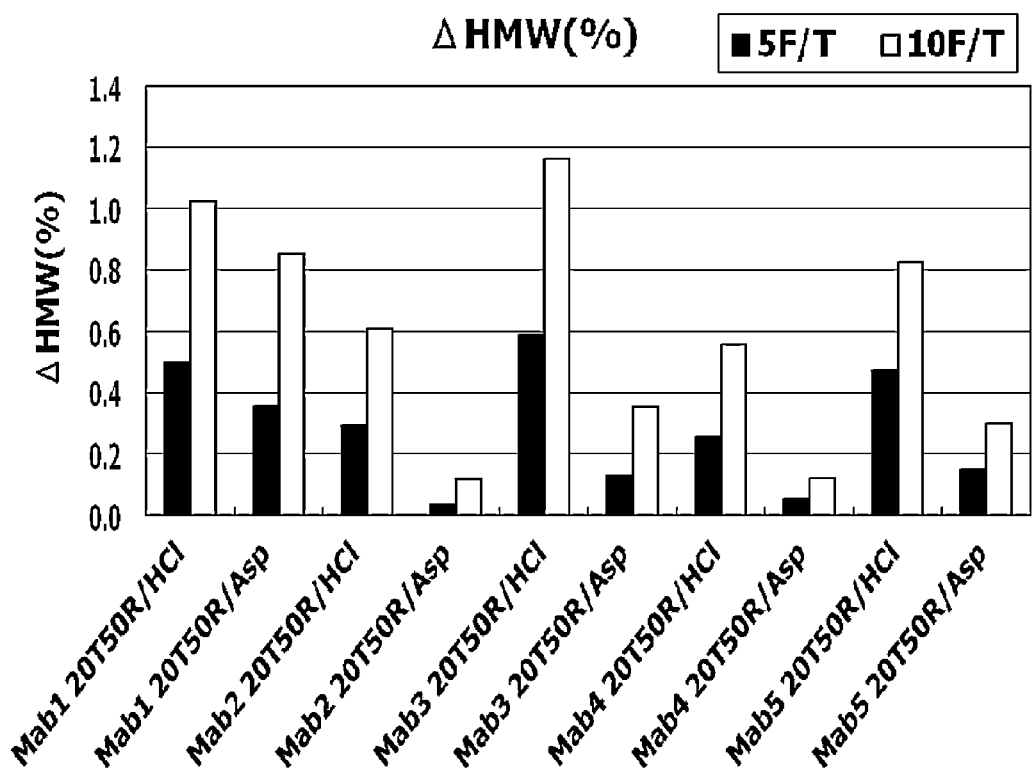
FIG. 22 is a graph plotted with time-dependent changes of the amount (%) of aggregate during freeze-thawing (between −20° C. and room temperature) of Mab1, Mab2, Mab3, Mab4, and Mab5 on the vertical axis.

The result on the increased amount (%) of aggregate in each formulation after freeze-thawing or liquid storage at 25° C. is shown in FIGS. 21 and 22. Comparison of the increased amounts of aggregate during liquid storage at 25° C. demonstrated that the stability was comparable between the Tris-aspartate/arginine-aspartate formulation and Tris-chloride/arginine-chloride (FIG. 21).

Meanwhile, comparison of the increased amounts of aggregate after freeze-thawing revealed that the stability with the Tris-aspartate/arginine-aspartate formulation was higher than that with the Tris-chloride/arginine-chloride formulation (FIG. 22). Thus, the stability in frozen condition of antibody was also demonstrated to be significantly improved by using aspartic acid instead of hydrochloric acid as a counter ion species in the Tris formulation.

[Example 8] Assessment of Stabilization Effect of Counter Ion Species to Tris Using Mab1, Mab2, and Mab3

As described in Example 7, the stability in frozen condition of antibody was demonstrated to be significantly improved when aspartic acid was used instead of hydrochloric acid as a counter ion species in the Tris formulation. Then, hydrochloric acid and aspartic acid were used as a counter ion species to Tris, and assessed for the liquid storage stability and freeze-thawing stability using Mab1, Mab2, and Mab3.

Samples were prepared as follows: Mab1, Mab2, and Mab3 were dialyzed against each dialysis buffer (Table 13) overnight. Then, each antibody solution was concentrated to 100 mg/ml or a higher concentration, and each dialysate was added thereto so that the final antibody concentration was adjusted to about 100 mg/ml. A list of the formulated solutions prepared as described above is shown in Table 14. Storage study at 25° C. and freeze-thawing study were carried out using each formulated solution. The freeze-thawing study was carried out in ten cycles of freezing at −20° C. followed by thawing at 25° C. (slow freeze-thawing). Following slow freeze-thawing, the amount of aggregate in each sample was calculated by the area percentage method using size exclusion chromatography (SEC).

TABLE 13

| No. | Sample | Dialysis buffer | pH |
|---|---|---|---|
| 35 | Mab1 | 50 mM Tris-Chloride | 6.5 |
| 36 | Mab1 | 50 mM Tris-Aspartate | |
| 37 | Mab2 | 50 mM Tris-Chloride | |
| 38 | Mab2 | 50 mM Tris-Aspartate | |
| 39 | Mab3 | 50 mM Tris-Chloride | |
| 40 | Mab3 | 50 mM Tris-Aspartate | |

TABLE 14

| No. | Sample | Formulation | pH | Mab concentration (mg/mL) |
|---|---|---|---|---|
| 35 | Mab1 | 50 mM Tris-Chloride | 6.5 | 100 |
| 36 | Mab1 | 50 mM Tris-Aspartate | | |
| 37 | Mab2 | 50 mM Tris-Chloride | | |
| 38 | Mab2 | 50 mM Tris-Aspartate | | |
| 39 | Mab3 | 50 mM Tris-Chloride | | |
| 40 | Mab3 | 50 mM Tris-Aspartate | | |

Figure 23:
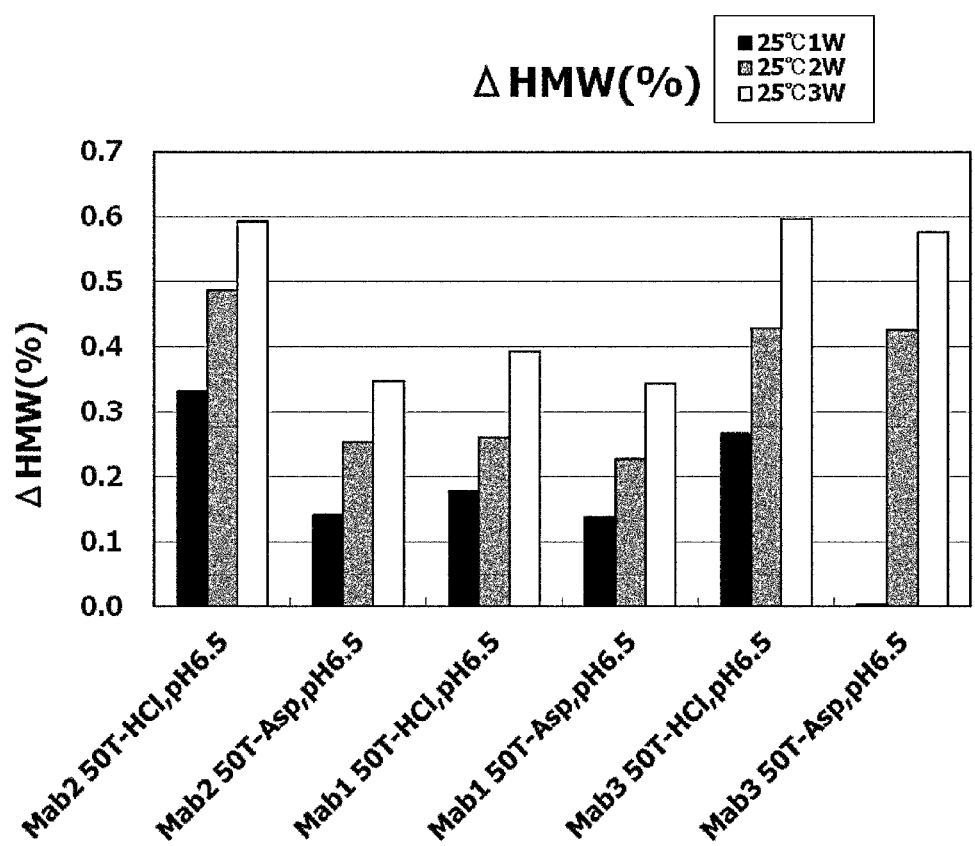
FIG. 23 is a graph plotted with time-dependent changes of the amount (%) of aggregate during storage of Mab1, Mab2, and Mab3 at 25° C. on the vertical axis.
Figure 24:
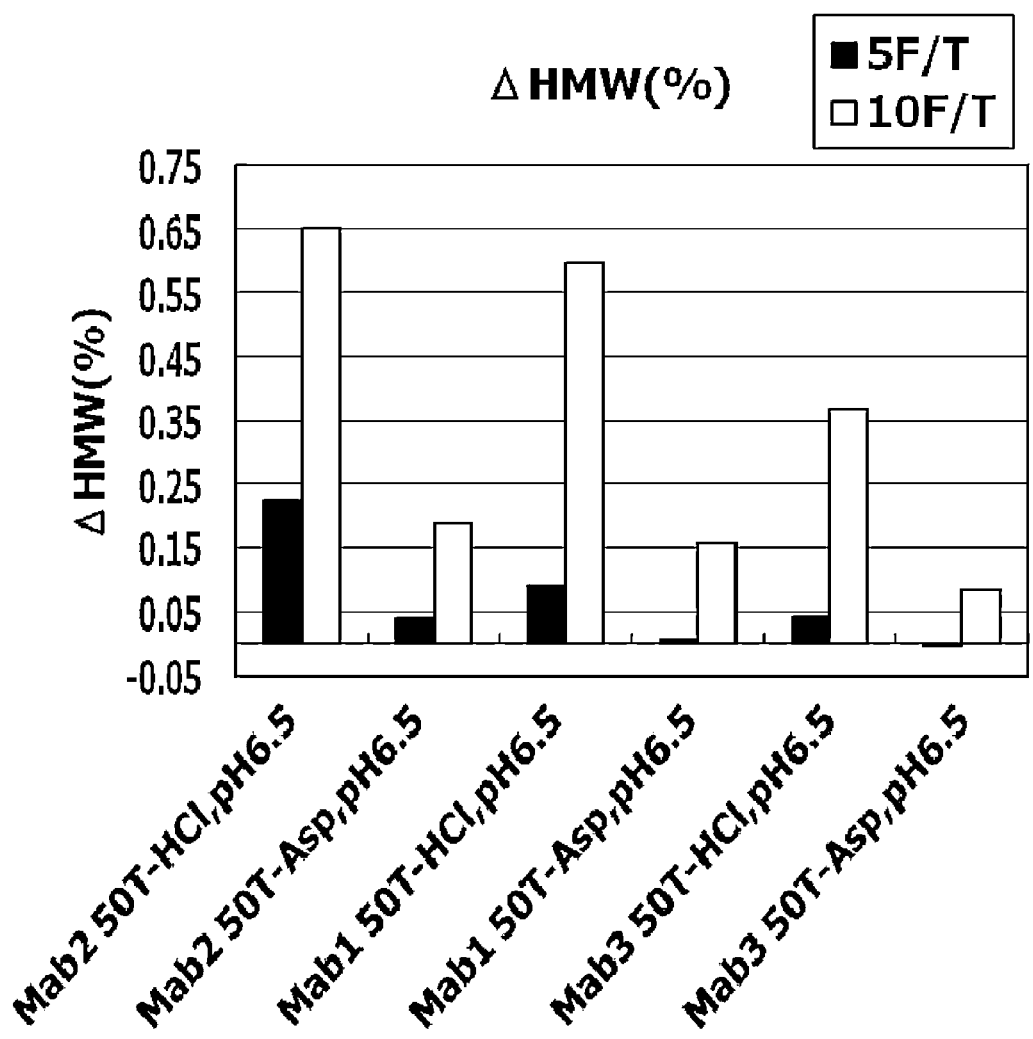
FIG. 24 is a graph plotted with time-dependent changes of the amount (%) of aggregate during freeze-thawing (between −20° C. and room temperature) of Mab1, Mab2, and Mab3 on the vertical axis.

The result on the increased amount (%) of aggregate after freeze-thawing or liquid storage at 25° C. in each formulation is shown in FIGS. 23 and 24. Comparison of the increased amounts of aggregate based on this result demonstrated that during both liquid storage at 25° C. and during freeze-thawing, the stability with the Tris-aspartate formulation was higher than that with the Tris-chloride formulation, and the stability during freeze-thawing was in particular two or more times higher. Thus, the antibody stability was also demonstrated to be significantly improved by using aspartic acid instead of hydrochloric acid as a counter ion species to Tris used as a buffering agent.

The invention claimed is:

1. A stable antibody-comprising formulation comprising a histidine-aspartate buffer or histidine glutamate-buffer, and arginine-aspartate or arginine-glutamate, wherein the pH of the formulation is 5.5 to 6.5 and wherein (a) the formulation does not substantially comprise a chloride ion and an acetate ion; (b) the concentration of the antibody in the formulation is 50 mg/mL or more; and (c) the antibody has been modified to have an isoelectric point (pI) of between 5.0 to 8.0, wherein the formulation is a liquid formulation.

2. The formulation of claim 1 comprising histidine aspartate buffer and arginine aspartate.

3. The formulation of claim 1 comprising a histidine glutamate buffer and arginine glutamate.

4. A stable antibody-comprising an anti-IL-6 receptor antibody, histidine-aspartate buffer or histidine-glutamate buffer, and arginine-aspartate or arginine-glutamate, wherein (a) the formulation does not substantially comprise a chloride ion and an acetate ion; (b) the concentration of the antibody in the formulation is 50 mg/mL or greater; and (c) the antibody has been modified to have an isoelectric point (pI) of between 5.0 to 8.0, wherein the formulation is a liquid formulation.

5. The formulation according to any one of claims 1-4, which additionally comprises a sugar.

6. The formulation according to any one of claims 1-4, wherein the antibody is a humanized antibody or a human antibody.

7. The formulation according to any one of claims 1-4, wherein the antibody concentration is 50 to 250 mg/ml.

8. The formulation according to any one of claims 1 to 4, wherein the viscosity of the liquid formulation is 30 mPa·s or less.

9. The formulation according to any one of claims 1 to 4, wherein the liquid formulation is stable at 2° C. to 8° C. for at least six months.

10. The formulation according to any one of claims 1 to 4, which has not been subjected to lyophilization during preparation of the formulation.

11. The formulation according to any one of claims 1 to 4, which is frozen stored at −30° C. to −10° C.

12. The formulation according to claim 1 or 4, wherein the buffer concentration is 5 to 100 mM.

13. The formulation according to claim 3, wherein the arginine concentration is 5 to 300 mM.

14. The formulation according to any one of claims 1 to 3, wherein the antibody is an anti-IL-6 receptor antibody.

15. The formulation according to any one of claims 1 to 4, which is for subcutaneous administration.

16. A method for suppressing aggregation formation during frozen storage of an antibody-comprising formulation by using aspartic acid or glutamic acid as a counter ion species to a histidine buffer in the formulation, wherein the pH of the formulation is 5.5 to 6.5, and wherein the concentration of the antibody in the formulation is 50 mg/mL or more.

17. A method for suppressing aggregation formation during liquid storage of an antibody-comprising formulation by using aspartic acid or glutamic acid as a counter ion species to a histidine buffer in the formulation, wherein the pH of the formulation is 5.5 to 6.5, and wherein the concentration of the antibody in the formulation is 50 mg/mL or more.

* * * * *

UNITED STATES PATENT AND TRADEMARK OFFICE
CERTIFICATE OF CORRECTION

PATENT NO. : 10,022,319 B2
APPLICATION NO. : 13/522848
DATED : July 17, 2018
INVENTOR(S) : Igawa et al.

It is certified that error appears in the above-identified patent and that said Letters Patent is hereby corrected as shown below:

Columns 31 and 32, Claim 4, please replace with the amended claim below:
A stable antibody-comprising formulation comprising an anti-IL-6 receptor antibody, histidine-aspartate buffer or histidine-glutamate buffer, and arginine-aspartate or arginine-glutamate, wherein (a) the formulation does not substantially comprise a chloride ion and an acetate ion; (b) the concentration of the antibody in the formulation is 50 mg/mL or greater; and (c) the antibody has been modified to have an isoelectric point (pI) of between 5.0 to 8.0, wherein the formulation is a liquid formulation.

Signed and Sealed this
Sixth Day of October, 2020

Andrei Iancu
*Director of the United States Patent and Trademark Office*

SEQUENCE LISTING

<160> NUMBER OF SEQ ID NOS: 4

<210> SEQ ID NO 1
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 1

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
```

```
                    355                 360                 365
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 2
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 2

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 3
```

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
```

```
                    420               425               430
Ala Leu His Asn His Tyr Thr Gln Lys Ser Leu Ser Leu Ser Pro Gly
            435               440               445
Lys

<210> SEQ ID NO 4
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```